(12) United States Patent
Blangy

(10) Patent No.: US 8,940,798 B2
(45) Date of Patent: Jan. 27, 2015

(54) COMPOUNDS USEFUL FOR TREATING AND/OR PREVENTING DISEASE-ASSOCIATED BONE LOSS

(71) Applicants: Centre National de al Recherche Scientifique (CNRS), Paris (FR); Universite Montpellier 2 Sciences et Techniques, Montpellier (FR)

(72) Inventor: Anne Blangy, Montpellier (FR)

(73) Assignees: Centre National de la Recherche Scientifique (CNRS), Paris (FR); Universite Montpellier 2 Sciences et Techniques, Montpellier (FR)

( * ) Notice: Subject to any disclaimer, the term of this patent is extended or adjusted under 35 U.S.C. 154(b) by 0 days.

(21) Appl. No.: 13/668,714

(22) Filed: Nov. 5, 2012

(65) Prior Publication Data
US 2013/0165523 A1 Jun. 27, 2013

Related U.S. Application Data

(60) Provisional application No. 61/555,721, filed on Nov. 4, 2011.

(51) Int. Cl.
| | | |
|---|---|---|
| *A61K 31/04* | (2006.01) | |
| *A61K 31/055* | (2006.01) | |
| *A61K 31/02* | (2006.01) | |
| *A61K 31/03* | (2006.01) | |
| *A61K 31/10* | (2006.01) | |
| *A61K 31/145* | (2006.01) | |
| *A61K 31/18* | (2006.01) | |

(52) U.S. Cl.
CPC ............... *A61K 31/145* (2013.01); *A61K 31/18* (2013.01)
USPC ........... 514/741; 514/758; 514/751; 514/708; 514/740

(58) Field of Classification Search
None
See application file for complete search history.

(56) References Cited

U.S. PATENT DOCUMENTS

2011/0237907 A1  9/2011  Kirsch et al.

FOREIGN PATENT DOCUMENTS

WO   WO-2005/064007 A2   7/2005

OTHER PUBLICATIONS

Vives et al., The Rac1 exchange factor Dock5 is essential for bone resorption by osteoclasts, Journal of Bone and Mineral Research (2011), 26(5), 1099-1110.*
Van Sickle et al., Lipids, vol. 27, No. 3, pp. 157-160, 1992.*
Abassi et al., "Tyrosine 221 in Crk regulates adhesion-dependent membrane localization of Crk and Rac and activation of Rac signaling," The EMBO Journal, vol. 21, No. 17, 2002, pp. 4571-4582.
Andre et al., "A Multiwell Assay to Isolate Compounds Inhibiting the Assembly of the Prokaryotic RNA Polymerase," ASSAY and Drug Development Technologies, vol. 2, No. 6, 2004, pp. 629-635.
Battini et al., "A human cell-surface receptor for xenotropic and polytropic murine leukemia viruses: Possible role in G protein-coupled signal transduction," Proc. Natl. Acad. Sci. USA, vol. 96, Feb. 1999, pp. 1385-1390.
Blair and Schlesinger, The Mechanism of Osteoclast Acidification, Chapter 13, 1992, pp. 259-287.
Blangy et al., "Identification of TRIO-GEFD1 chemical inhibitors using the yeast exchange assay," Biol. Cell, vol. 96, No. 9, 2006, pp. 511-522.
Bouquier et al., "A Cell Active Chemical GEF Inhibitor Selectively Targets the Trio/RhoG/Rac1 Signaling Pathway," Chemistry and Biology, vol. 16, 2009, pp. 657-666.
Brazier et al., "Expression Profile of RhoGTPases and RhoGEFs During RANKL-Stimulated Osteoclastogenesis: Identification of Essential Genes in Osteoclasts," Journal of Bone and Mineral Research, vol. 21, No. 9, 2006, pp. 1387-1398.
Brazier et al., "The Rho GTPase Wrch 1 regulates osteoclast precursor adhesion and migration," The International Journal of Biochemistry & Cell Biology, vol. 41, 2009, pp. 1391-1401.
Bulk, et al., Adjuvant Therapy with Small Hairpin RNA Interference Prevents Non-Small Cell Lung Cancer Metastasis Development in Mice, Cancer Res., vol. 68, No. 6, 2008, pp. 1896-1904.
Carano et al., "Bisphosphonates Directly Inhibit the Bone Resorption Activity of Isolated Avian Osteoclasts in Vitro," J. Clin. Invest., vol. 85, Feb. 1990, pp. 456-461.
Choi et al., "ADAM8: A Novel Osteoclast Stimulating Factor," Journal of Bone and Mineral Research, vol. 16, Nov. 2001, pp. 814-822.
Coelho et al., "Interferon-$\alpha$ and -$\beta$ differentially regulate osteoclastogenesis: Role of differential induction of chemokine CXCL11 expression," PNAS, vol. 102, No. 33, Aug. 2005, pp. 11917-11922.
Cote et al., "GEF what? Dock 180 and related proteins help Rac to polarize cells in new ways," Trends in Cell biology, vol. 17, No. 8, 2007, pp. 383-393.
Cote et al., "Identification of an evolutionarily conserved superfamily of DOCK180-related proteins with guanine nucleotide exchange activity," Journal of Cell Science, vol. 115, 2002, pp. 4901-4913.
Edgar, "MUSCLE: multiple sequence alignment with high accuracy and high throughput," Nucleic Acids Research, vol. 32, No. 5, 2004, pp. 1792-1797.
Fukuda et al., "Regulation of Osteoclast Apoptosis and Motility by Small GTPase Binding Protein Rac1," Journal of Bone and Mineral Research, Vo. 20, No. 12, 2005, pp. 2245-2253.
Girotra et al., "The use of parathyroid hormone in the treatment of osteoporosis," Rev Endocr Metab Disord, vol. 7, 2006, pp. 113-121.
Gumienny et al., "CED-12/ELMO, a Novel Member of the CrkII/Dock180/Rac Pathway, Is Required for Phagocytosis and Cell Migration," Cell., vol. 107, Oct. 2001, pp. 27-41.
Ha et al., "Proteomic profile of osteoclast membrane proteins: Identification of $Na^+/H^+$ exchanger domain containing 2 and its role in osteoclast fusion," Proteomics, vol. 8, 2008, pp. 2625-2639.
Kim et al., NFATc1 Induces Osteoclast Fusion Via Up-Regulation of Atp6v0d2 and the Dendric Cell- Specific Transmembrane Protin (DC-STAMP), Molecular Endocrinology, vol. 22, No. 1, 2008, pp. 176-185.

(Continued)

*Primary Examiner* — Svetlana M Ivanova
(74) *Attorney, Agent, or Firm* — Foley & Lardner LLP

(57) ABSTRACT

The present invention concerns a method for treating and/or preventing a disease in a subject comprising the step of administrating an effective amount of a compound of formula I to a subject in need thereof.

8 Claims, 23 Drawing Sheets

(56) References Cited

OTHER PUBLICATIONS

Lassaux et al., "Residues in the Murine Leukemia Virus Capsid That Differentially Govern Resistance to Mouse *Fv1* and Human *Ref1* Restrictions," Journal of Virology, vol. 79, No. 10, May 2005, pp. 6560-6564.

Needleman et al. "A General Method Applicable to the Search for Similarities in the Amino Acid Sequence of Two Proteins," J. Mol. Biol., vol. 48, 1970, pp. 443-453.

Omi et al., "Mutation of DockS, a member of the guanine exchange factor Dock180 superfamily, in the rupture of lens cataract mouse," Experimental Eye Research, vol. 86, 2008, pp. 828-834.

Parrini et al., "Pak1 Kinase Homodimers Are Autoinhibited in *trans* and Dissociated upon Activation by Cdc42 and Rac1," Molecular Cell, vol. 9, Jan. 2002, pp. 73-83.

Pearson et al., "Improved tools for biological sequence comparison," Proc. Natl. Acad. Sci. USA, vol. 85, Apr. 1988, pp. 2444-2448.

Razzouk, et al., "Rac-GTPase, osteoclast cytoskeleton and bone resorption," European Journal of Cell Biology, vol. 78, Apr. 1999, pp. 249-255.

Schlesinger and Blair, Bisphosphonates, Chapter 18, 1992, pp. 397-417.

Toledo et al., "The yeast exchange assay, a new complementary method to screen for Dbl-like protein specificity: identification of a novel RhoA exchange factor," FEBS Letters, vol. 480, 2000, pp. 287-292.

Vaananen et al., "Evidence for the Presence of a Proton Pump of the Vacuolar $H^+$-ATPhase Type in the Ruffled Borders of Osteoclasts," The Journal of Cell Biology, vol. 111, Sep. 1990, pp. 1305-1311.

XP002499980, Database UniProt [Online], Jul. 1, 2008, 3 Pages.
XP002499981, Database UniProt [Online]Jul. 1, 2008, 3 Pages
XP002499982, Database UniProt [Online] Aug. 31, 2004, 21 Pages.
XP002499983, Database UniProt [Online] Nov. 1, 1997, 14 Pages.

\* cited by examiner

Fig. 2A    Fig. 2B
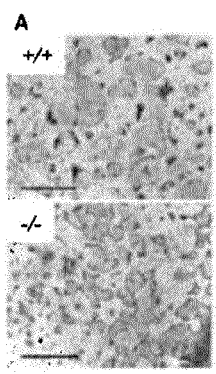
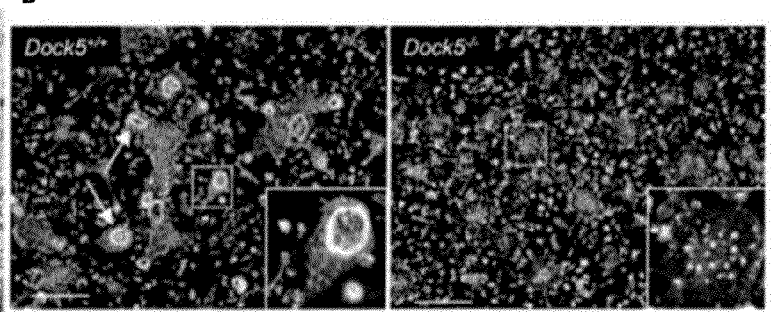
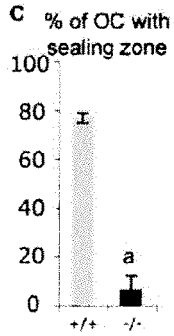
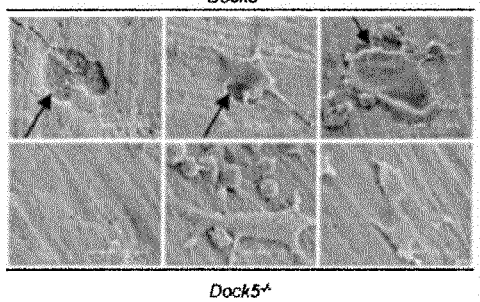
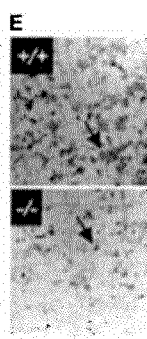
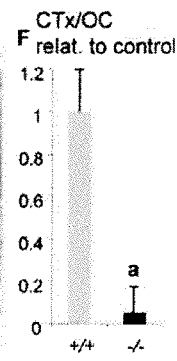
Fig. 2C        Fig. 2D        Fig. 2E    Fig. 2F Fig. 3A
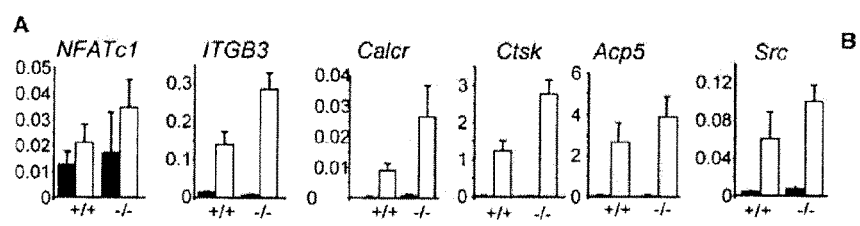
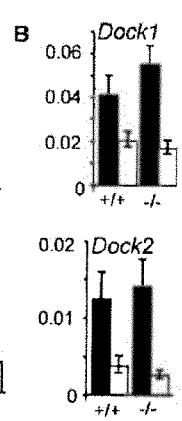
Fig. 3B
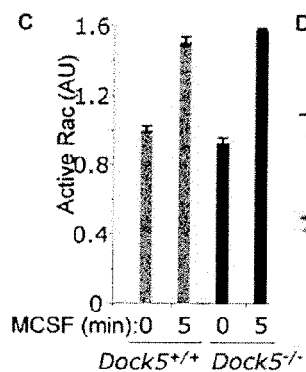
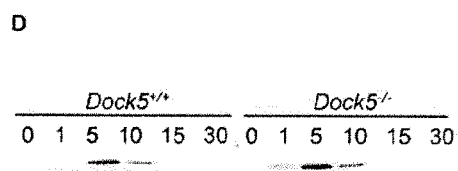
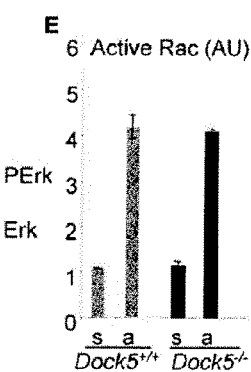
Fig. 3C          Fig. 3D          Fig. 3E

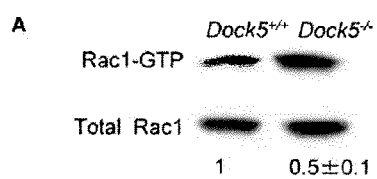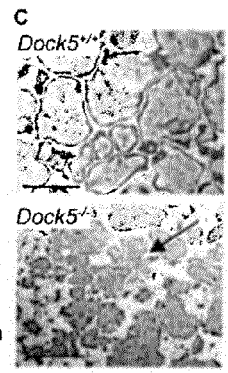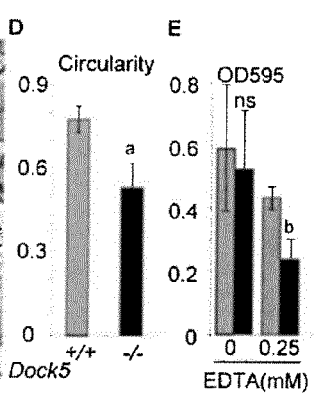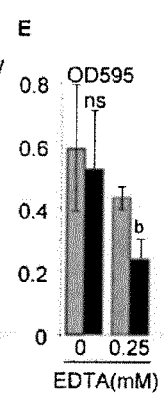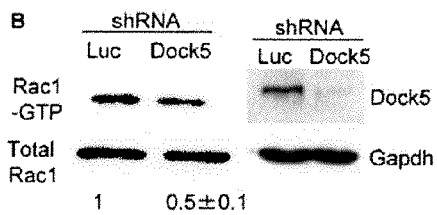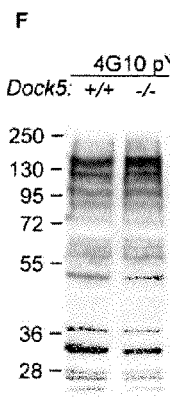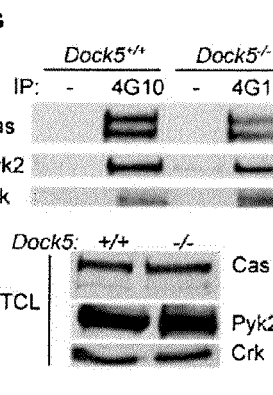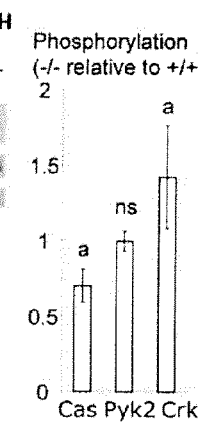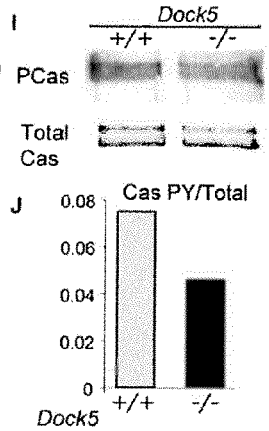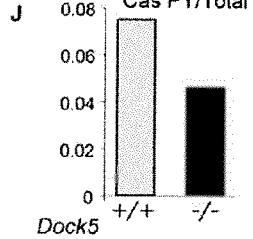
Fig. 4A  Fig. 4C  Fig. 4D  Fig. 4E
Fig. 4B
Fig. 4F  Fig. 4G  Fig. 4H  Fig. 4I Fig. 5A    Fig. 5B    Fig. 5C
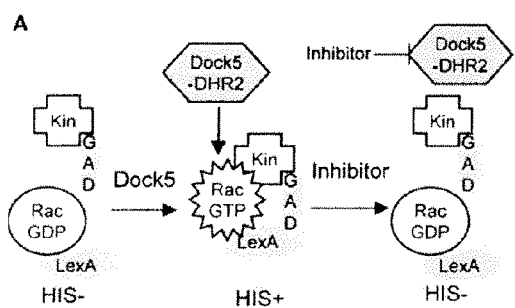 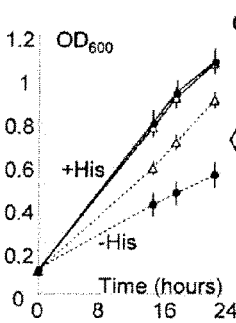 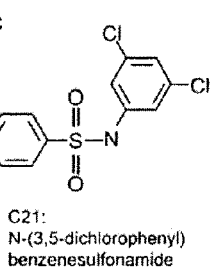
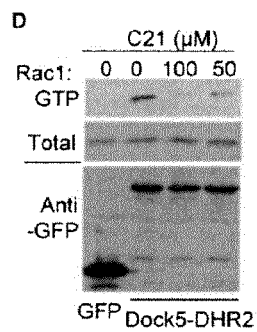 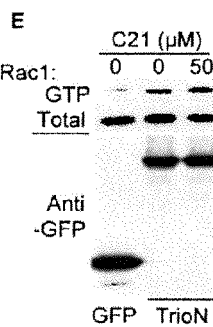 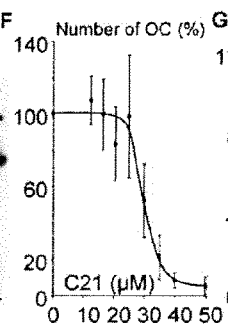 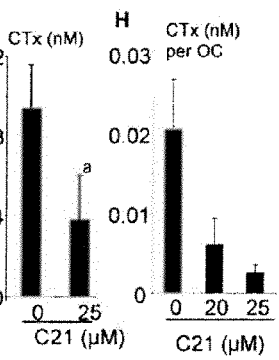
Fig. 5D    Fig. 5E    Fig. 5F    Fig. 5G    Fig. 5H Fig. 6A  Fig. 6B
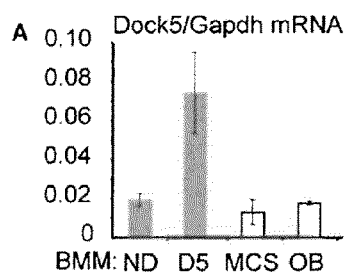
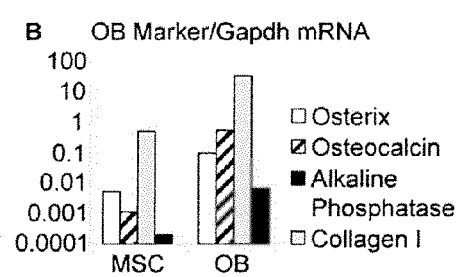
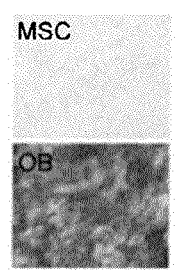
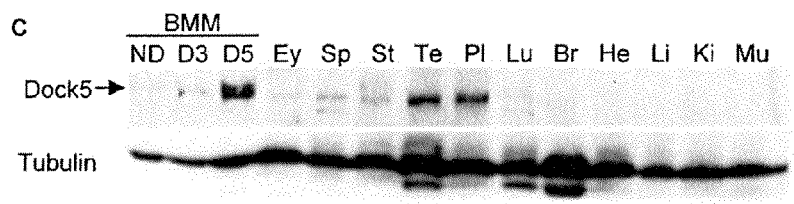
Fig. 6C
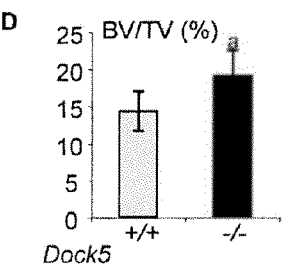
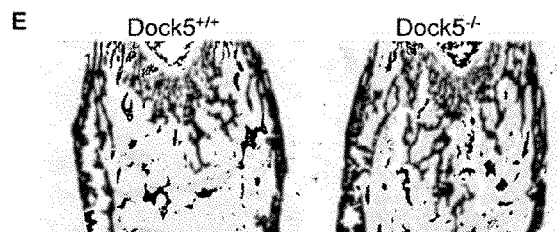
Fig. 6D  Fig. 6E
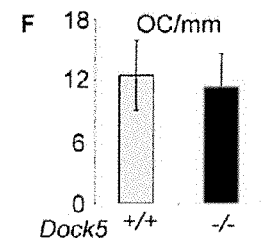
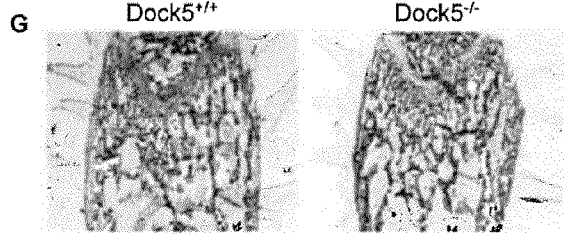
Fig. 6F  Fig. 6G Correlation between Score and BV/TV :
-0.6957 ± 0.3, significantly different from
0, (p=0.0307)
Spearman r = -1 (95% CI), p<0.0001
n = 24

Correlation between Score and BV/TV :
-0.6957 ± 0.3, significantly different from
0, (p=0.0307)
Spearman r = -1 (95% CI), p<0.0001
n = 24

SEQUENCE LISTING

<160> NUMBER OF SEQ ID NOS: 13

<210> SEQ ID NO 1
<211> LENGTH: 1868
<212> TYPE: PRT
<213> ORGANISM: Mus musculus

<400> SEQUENCE: 1

```
Met Ala Arg Trp Ile Pro Thr Lys Arg Gln Lys Tyr Gly Val Ala Ile
1               5                   10                  15

Tyr Asn Tyr Asn Ala Ser Gln Asp Val Glu Leu Ser Leu Gln Ile Gly
            20                  25                  30

Asp Thr Val His Ile Leu Glu Met Tyr Glu Gly Trp Tyr Arg Gly Tyr
        35                  40                  45

Ala Leu Gln Asn Arg Ser Lys Lys Gly Ile Phe Pro Glu Thr Tyr Ile
    50                  55                  60

His Leu Lys Glu Ala Thr Val Glu Asp Gly Gly Gln His Glu Thr Val
65                  70                  75                  80

Ile Pro Gly Glu Leu Pro Leu Val Gln Glu Leu Thr Asn Thr Leu Arg
                85                  90                  95

Glu Trp Ala Val Ile Trp Arg Lys Leu Tyr Val Asn Asn Lys Val Thr
            100                 105                 110

Leu Phe Arg Gln Leu Gln Gln Met Thr Tyr Ser Leu Ile Glu Trp Arg
        115                 120                 125

Ser Gln Ile Leu Ser Gly Thr Leu Pro Lys Asp Glu Leu Ala Glu Leu
    130                 135                 140

Lys Lys Lys Val Thr Ala Lys Ile Asp His Gly Asn Arg Met Leu Gly
145                 150                 155                 160

Leu Asp Leu Val Val Arg Asp Asp Asn Gly Asn Ile Leu Asp Pro Asp
                165                 170                 175

Glu Thr Ser Thr Val Ala Leu Phe Arg Ala His Glu Val Ala Ser Lys
            180                 185                 190

Arg Ile Glu Glu Lys Ile Gln Glu Glu Lys Ser Ile Leu Gln Asn Leu
        195                 200                 205

Asp Leu Arg Gly Gln Ala Ile Phe Ser Thr Val His Thr Tyr Gly Leu
    210                 215                 220

Tyr Val Asn Phe Lys Asn Phe Val Cys Asn Ile Gly Glu Asp Ala Glu
225                 230                 235                 240

Leu Phe Ile Ala Leu Tyr Asp Pro Asp Gln Ser Thr Phe Ile Ser Glu
                245                 250                 255

Asn Tyr Leu Ile Arg Trp Gly Ser Asn Gly Met Pro Lys Glu Ile Glu
            260                 265                 270

Lys Leu Asn Asn Leu Gln Ala Val Phe Thr Asp Leu Ser Ser Thr Asp
        275                 280                 285

Leu Ile Arg Pro Arg Ile Ser Leu Val Cys Gln Ile Val Arg Val Gly
    290                 295                 300

Arg Met Glu Leu Lys Glu Gly Lys Lys His Thr Cys Gly Leu Arg Arg
305                 310                 315                 320

Pro Phe Gly Val Ala Val Met Asp Ile Ser Asp Ile Val His Gly Lys
                325                 330                 335

Val Asp Asp Glu Glu Lys Gln His Phe Ile Pro Phe Gln Gln Ile Ala
            340                 345                 350

Met Glu Thr Tyr Ile Arg Gln Arg Gln Leu Ile Met Ser Pro Leu Ile
        355                 360                 365
```

```
Thr Ser His Val Ile Gly Glu Asn Glu Pro Leu Thr Ser Val Leu Asn
    370                 375                 380

Lys Val Ile Ala Ala Lys Glu Val Asn His Lys Gly Gln Gly Leu Trp
385                 390                 395                 400

Val Ser Leu Lys Leu Leu Pro Gly Asp Leu Thr Gln Val Gln Lys Asn
                405                 410                 415

Phe Ser His Leu Val Asp Arg Ser Thr Ala Ile Ala Arg Lys Met Gly
            420                 425                 430

Phe Pro Glu Ile Ile Leu Pro Gly Asp Val Arg Asn Asp Ile Tyr Val
        435                 440                 445

Thr Leu Ile His Gly Glu Phe Asp Lys Gly Lys Lys Thr Pro Lys
    450                 455                 460

Asn Val Glu Val Thr Met Ser Val Phe Asp Glu Gly Asn Leu Leu
465                 470                 475                 480

Glu Lys Ala Ile His Pro Gly Ala Gly Tyr Glu Gly Val Ser Glu Tyr
                485                 490                 495

Lys Ser Val Val Tyr Tyr Gln Val Lys Gln Pro Cys Trp Tyr Glu Thr
                500                 505                 510

Val Lys Val Phe Ile Ala Ile Glu Glu Val Thr Arg Cys His Ile Arg
                515                 520                 525

Phe Thr Phe Arg His Arg Ser Ser Gln Glu Ser Arg Asp Lys Ser Glu
    530                 535                 540

Arg Ala Phe Gly Val Ala Phe Val Lys Leu Met Asn Ala Asp Gly Thr
545                 550                 555                 560

Thr Leu Gln Asp Gly Arg His Asp Leu Val Val Tyr Lys Gly Asp Asn
                565                 570                 575

Lys Lys Met Glu Asp Ala Lys Tyr Tyr Leu Thr Leu Pro Gly Thr Lys
            580                 585                 590

Ala Glu Leu Glu Glu Lys Glu Leu Gln Ala Ser Lys Asn Pro Ser Val
        595                 600                 605

Phe Thr Pro Ser Lys Asp Ser Thr Lys Asp Ser Phe Gln Ile Ala Thr
    610                 615                 620

Leu Ile Cys Ser Thr Lys Leu Thr Gln Asn Val Asp Leu Leu Gly Leu
625                 630                 635                 640

Leu Asn Trp Arg Ser Asn Ser Gln Asn Ile Lys His Asn Leu Lys Lys
                645                 650                 655

Leu Met Glu Val Asp Gly Gly Glu Ile Val Lys Phe Leu Gln Asp Thr
            660                 665                 670

Leu Asp Ala Leu Phe Asn Ile Met Met Glu Met Ser Asp Asn Glu Thr
        675                 680                 685

Tyr Asp Phe Leu Val Phe Asp Ala Leu Val Phe Ile Ile Ser Leu Ile
    690                 695                 700

Gly Asp Ile Lys Phe Gln His Phe Asn Pro Val Leu Glu Thr Tyr Ile
705                 710                 715                 720

Tyr Lys His Phe Ser Ala Thr Leu Ala His Val Lys Leu Ser Lys Val
                725                 730                 735

Leu Asn Phe Tyr Val Ala Asn Ala Glu Asp Pro Ser Lys Thr Glu Leu
            740                 745                 750

Leu Phe Ala Ala Leu Lys Ala Leu Lys Tyr Leu Phe Arg Phe Ile Ile
        755                 760                 765

Gln Ser Arg Val Leu Tyr Leu Arg Phe Tyr Gly Gln Ser Glu Asp Gly
    770                 775                 780

Asp Glu Phe Asn Asp Ser Ile Arg Gln Leu Phe Leu Ala Phe Asn Thr
```

```
                785                 790                 795                 800
Leu Met Asp Arg Pro Leu Glu Glu Ala Val Lys Ile Lys Gly Ala Ala
                805                 810                 815

Leu Lys Tyr Leu Pro Ser Ile Ile Asn Asp Val Lys Leu Val Phe Asp
                820                 825                 830

Pro Met Glu Leu Ser Val Leu Phe Cys Lys Phe Ile Gln Ser Ile Pro
                835                 840                 845

Asp Asn Gln Leu Val Arg Gln Lys Leu Asn Cys Met Thr Lys Ile Val
    850                 855                 860

Glu Ser Ser Leu Phe Gln Gln Ala Glu Cys Arg Glu Val Leu Leu Pro
865                 870                 875                 880

Leu Leu Thr Asp Gln Leu Ser Gly Gln Leu Asp Asp His Ser Thr Lys
                885                 890                 895

Pro Asp His Glu Ala Ser Ser Gln Leu Leu Ser Asn Ile Leu Glu Val
                900                 905                 910

Leu Asp Arg Thr Asp Val Gly Pro Thr Ser Ala His Val Gln Leu Ile
                915                 920                 925

Met Glu Arg Leu Leu Arg Arg Ile Asn Arg Thr Val Ile Gly Met Ser
    930                 935                 940

Arg Gln Ser Pro His Ile Gly Ser Phe Val Ala Cys Met Ile Ala Val
945                 950                 955                 960

Leu Arg Gln Met Glu Asp Ser His Tyr Ser His Tyr Ile Ser Thr Phe
                965                 970                 975

Lys Thr Arg Gln Asp Ile Ile Asp Phe Leu Met Glu Thr Phe Ile Met
                980                 985                 990

Phe Lys Asp Leu Ile Gly Lys Asn  Val Tyr Ala Lys Asp Trp Met Val
                995                 1000                1005

Met Asn  Met Thr Gln Asn Arg  Val Phe Leu Arg Ala  Ile Asn Gln
    1010                1015                1020

Phe Ala  Glu Val Leu Thr Lys  Ser Phe Met Asp Gln  Ala Ser Phe
    1025                1030                1035

Glu Leu  Gln Leu Trp Asn Asn  Tyr Phe His Leu Ala  Val Ala Phe
    1040                1045                1050

Leu Thr  His Glu Ser Leu Gln  Leu Glu Thr Phe Ser  Glu Ala Lys
    1055                1060                1065

Arg Asn  Lys Ile Val Lys Lys  Tyr Gly Asp Met Arg  Lys Glu Ile
    1070                1075                1080

Gly Phe  Arg Ile Arg Asp Met  Trp Tyr Asn Leu Gly  Pro His Lys
    1085                1090                1095

Ile Lys  Phe Ile Pro Ser Met  Val Gly Pro Ile Leu  Glu Val Thr
    1100                1105                1110

Leu Thr  Pro Glu Val Glu Leu  Arg Lys Ala Thr Ile  Pro Ile Phe
    1115                1120                1125

Phe Asp  Met Met Gln Cys Glu  Phe Asn Leu Ser Gly  Asn Gly Asn
    1130                1135                1140

Phe His  Met Phe Glu Asn Glu  Leu Ile Thr Lys Leu  Asp Gln Glu
    1145                1150                1155

Val Glu  Gly Gly Arg Gly Asp  Glu Gln Tyr Lys Val  Leu Leu Glu
    1160                1165                1170

Lys Leu  Leu Leu Glu His Cys  Arg Lys His Lys Tyr  Leu Ala Asn
    1175                1180                1185

Ser Gly  Glu Ala Phe Ala Phe  Leu Val Ser Ser Leu  Leu Glu Asn
    1190                1195                1200
```

```
Leu Leu Asp Tyr Arg Thr Ile Ile Ile His Asp Glu Ser Lys Glu
1205                1210                1215

Asn Arg Met Ser Cys Thr Val Asn Val Leu Asn Phe Tyr Lys Asp
1220                1225                1230

Lys Lys Arg Glu Asp Ile Tyr Ile Arg Tyr Leu Tyr Lys Leu Arg
1235                1240                1245

Asp Leu His Arg Asp Cys Glu Asn Tyr Thr Glu Ala Ala Tyr Thr
1250                1255                1260

Leu Leu Leu His Ala Glu Leu Leu Gln Trp Ser Asp Lys Pro Cys
1265                1270                1275

Val Pro His Leu Leu Gln Arg Asp Ser Tyr Tyr Val Tyr Thr Gln
1280                1285                1290

Gln Glu Leu Lys Glu Lys Leu Tyr Gln Glu Ile Ile Ser Tyr Phe
1295                1300                1305

Asp Lys Gly Lys Met Trp Glu Lys Ala Ile Lys Leu Ser Lys Glu
1310                1315                1320

Leu Ala Glu Thr Tyr Glu Ser Lys Val Phe Asp Tyr Glu Gly Leu
1325                1330                1335

Gly Ser Leu Leu Lys Lys Arg Ala Leu Phe Tyr Glu Asn Ile Ile
1340                1345                1350

Lys Ala Met Arg Pro Gln Pro Glu Tyr Phe Ala Val Gly Tyr Tyr
1355                1360                1365

Gly Gln Gly Phe Pro Ser Phe Leu Arg Asn Lys Ile Phe Ile Tyr
1370                1375                1380

Arg Gly Lys Glu Tyr Glu Arg Arg Glu Asp Phe Ser Leu Arg Leu
1385                1390                1395

Leu Thr Gln Phe Pro Asn Ala Glu Lys Met Thr Ser Thr Thr Pro
1400                1405                1410

Pro Gly Glu Asp Ile Lys Ser Ser Pro Lys Gln Tyr Leu Gln Cys
1415                1420                1425

Phe Thr Val Lys Pro Val Met Ser Leu Pro Pro Ser Tyr Lys Asp
1430                1435                1440

Lys Pro Val Pro Glu Gln Ile Leu Asn Tyr Tyr Arg Ala Asn Glu
1445                1450                1455

Val Gln Gln Phe Ser Tyr Ser Arg Pro Phe Arg Lys Gly Glu Lys
1460                1465                1470

Asp Pro Glu Asn Glu Phe Ala Thr Met Trp Ile Glu Arg Thr Thr
1475                1480                1485

Tyr Arg Thr Ala Tyr Thr Phe Pro Gly Ile Leu Lys Trp Phe Glu
1490                1495                1500

Ala Lys Glu Ile Ser Val Glu Glu Ile Ser Pro Leu Glu Asn Ala
1505                1510                1515

Ile Glu Thr Met Glu Leu Thr Asn Glu Arg Val Ser Asn Cys Val
1520                1525                1530

Gln Gln His Ala Trp Asp His Ser Leu Ser Val His Pro Leu Ser
1535                1540                1545

Met Leu Leu Ser Gly Ile Val Asp Pro Ala Val Met Gly Gly Phe
1550                1555                1560

Ser Asn Tyr Glu Lys Ala Phe Phe Thr Glu Lys Tyr Leu Gln Glu
1565                1570                1575

His Pro Glu Asp Gln Glu Lys Val Glu Leu Leu Lys Arg Leu Ile
1580                1585                1590
```

```
Ala Leu Gln Ile Pro Leu Leu Thr Glu Gly Ile Arg Ile His Gly
1595                1600                1605

Glu Lys Leu Thr Glu Gln Leu Lys Pro Leu His Ala Arg Leu Ser
1610                1615                1620

Ser Cys Phe Arg Glu Leu Lys Glu Lys Val Glu Lys Leu Tyr Gly
1625                1630                1635

Val Ile Thr Leu Pro Pro Ser Met Thr Glu Arg Lys Pro Ser Arg
1640                1645                1650

Ala Gly Ser Met Val Leu Pro Tyr Ile Leu Ser Ser Thr Leu Arg
1655                1660                1665

Arg Leu Ser Val Thr Ser Val Ala Ser Ser Val Ile Ser Thr Ser
1670                1675                1680

Ser Asn Ser Ser Asp Asn Ala Ser Ser Arg Pro Gly Ser Asp Gly
1685                1690                1695

Ser Ile Leu Glu Pro Leu Phe Glu Arg Arg Ala Ser Ser Gly Ala
1700                1705                1710

Arg Val Glu Asp Leu Pro Pro Lys Glu Asp Ser Glu Asn Arg Ile
1715                1720                1725

Ser Lys Phe Lys Arg Lys Asp Trp Asn Leu Ser Lys Ser Gln Val
1730                1735                1740

Ile Ala Glu Lys Ala Pro Glu Pro Asp Val Met Ser Pro Gly Lys
1745                1750                1755

Lys Thr Gln Arg Pro Lys Ser Leu Gln Leu Val Asp Ser Arg Leu
1760                1765                1770

Thr Pro Phe His Ser Pro Ser Pro Leu Gln Ser Thr Ala Leu Ser
1775                1780                1785

Pro Pro Pro Leu Thr Pro Lys Ala Thr Arg Thr Leu Ser Ser Pro
1790                1795                1800

Ser Leu Gln Thr Asp Gly Leu Thr Ala Ser Val Pro Pro Pro Pro
1805                1810                1815

Pro Pro Lys Ser Lys Pro Tyr Glu Ser Ser Gln Arg Asn Ser Ala
1820                1825                1830

Glu Ile Ala Pro Pro Leu Pro Val Arg Arg Asp Ser Lys Ala Pro
1835                1840                1845

Pro Pro Pro Pro Pro Lys Ala Arg Lys Ser Gly Ile Leu Ser Ser
1850                1855                1860

Glu Pro Gly Ser Gln
1865

<210> SEQ ID NO 2
<211> LENGTH: 20
<212> TYPE: DNA
<213> ORGANISM: artificial
<220> FEATURE:
<223> OTHER INFORMATION: Calcitonin receptor primer

<400> SEQUENCE: 2
ggctgtgttt accgacgagc                                              20

<210> SEQ ID NO 3
<211> LENGTH: 20
<212> TYPE: DNA
<213> ORGANISM: artificial
<220> FEATURE:
<223> OTHER INFORMATION: Calcitonin receptor primer

<400> SEQUENCE: 3
```
caagcacgcg gacaatgttg                                          20

<210> SEQ ID NO 4
<211> LENGTH: 20
<212> TYPE: DNA
<213> ORGANISM: artificial
<220> FEATURE:
<223> OTHER INFORMATION: Dock1 primer

<400> SEQUENCE: 4
tcagcttcag cattcagccc                                          20

<210> SEQ ID NO 5
<211> LENGTH: 20
<212> TYPE: DNA
<213> ORGANISM: artificial
<220> FEATURE:
<223> OTHER INFORMATION: Dock1 primer

<400> SEQUENCE: 5
actgcacgat tccagagtcc                                          20

<210> SEQ ID NO 6
<211> LENGTH: 20
<212> TYPE: DNA
<213> ORGANISM: artificial
<220> FEATURE:
<223> OTHER INFORMATION: Dock2 primer

<400> SEQUENCE: 6
agccttgcat ctcctgtggc                                          20

<210> SEQ ID NO 7
<211> LENGTH: 20
<212> TYPE: DNA
<213> ORGANISM: artificial
<220> FEATURE:
<223> OTHER INFORMATION: Dock2 primer

<400> SEQUENCE: 7
catgcgtccc ttggatgctg                                          20

<210> SEQ ID NO 8
<211> LENGTH: 20
<212> TYPE: DNA
<213> ORGANISM: artificial
<220> FEATURE:
<223> OTHER INFORMATION: Osteocalcin primer

<400> SEQUENCE: 8
gcgctctgtc tctctgacct                                          20

<210> SEQ ID NO 9
<211> LENGTH: 20
<212> TYPE: DNA
<213> ORGANISM: artificial
<220> FEATURE:
<223> OTHER INFORMATION: Osteocalcin primer

<400> SEQUENCE: 9
gccggagtct gttcactacc                                          20

<210> SEQ ID NO 10
<211> LENGTH: 20
<212> TYPE: DNA
<213> ORGANISM: artificial

```
<220> FEATURE:
<223> OTHER INFORMATION: Alkaline Phosphatase primer

<400> SEQUENCE: 10
aatgccctga aactccaaaa                                              20

<210> SEQ ID NO 11
<211> LENGTH: 20
<212> TYPE: DNA
<213> ORGANISM: artificial
<220> FEATURE:
<223> OTHER INFORMATION: Alkaline Phosphatase primer

<400> SEQUENCE: 11
aggggaattt gtccatctcc                                              20

<210> SEQ ID NO 12
<211> LENGTH: 20
<212> TYPE: DNA
<213> ORGANISM: artificial
<220> FEATURE:
<223> OTHER INFORMATION: Collagen I  primer

<400> SEQUENCE: 12
tgttcagctt tgtggacctc                                              20

<210> SEQ ID NO 13
<211> LENGTH: 20
<212> TYPE: DNA
<213> ORGANISM: artificial
<220> FEATURE:
<223> OTHER INFORMATION: Collagen I  primer

<400> SEQUENCE: 13
tcaagcatac ctcgggtttc                                              20
```

COMPOUNDS USEFUL FOR TREATING AND/OR PREVENTING DISEASE-ASSOCIATED BONE LOSS

FIELD OF THE INVENTION

The invention relates to the field of diseases associated with bone loss, and more specifically to new compounds useful for treating and/or preventing diseases associated with bone loss.

BACKGROUND OF THE INVENTION

Bone is a dynamic tissue that is continually remodeled throughout life depending on factors such as nutrition and the load the bone must carry. Normal bone formation depends on the delicate balance between new bone addition and old bone resorption. Bone formation is based on the deposition of bone matrix by osteoblasts and bone resorption and more specifically mineralized tissue, chiefly calcium carbonate and calcium phosphate resorption in vertebrates is achieved by osteoclasts. Typically, in a normal adult, about 5-10% of bone is replaced by these processes annually.

These osteoclasts are multinucleated cells of up to 400 µm related to macrophage and other cells that develop from monocyte cells, which are actively motile cells that migrate along the surface of bone. Like macrophage, osteoclasts are derived from haematopoietic progenitor cells. The bone resorption is initiated when an osteoclast attaches to the surface of mineralized bone, forms a tight "sealing zone" and secretes necessary acids and proteases that initiate the resorption of mineralized tissue from the bone. After a period of several hours to days, the osteoclast detaches from the bone, leaving a pit on the bone surface. Under normal conditions, the pit is a target for osteoblasts, which deposit a material that ultimately becomes new bone.

Bone loss can appear when the bone resorptive process is dominant over the bone formative process. Diseases associated with bone loss are usually accompanied by increased osteoclast activation. Such diseases include any bone loss resulting notably from an estrogen deficiency after the menopause but not only and comprise osteoporosis, osteopenia due to bone metastases, periarticular erosions in rheumatoid arthritis, primary hyperparathyroidism, hypercalcemia of malignancy, Paget's disease of bone, periodontal disease, immobilization induced osteopenia, and glucocorticoid treatment.

As an example, there are currently 20 million people with detectable fractures of the vertebrae due to osteoporosis in the United States. In addition, there are 250,000 hip fractures per year attributed to osteoporosis. This clinical situation is associated with a 12% mortality rate within the first two years, while 30% of the patients require nursing home care after the fracture.

The available treatments of osteolytic diseases are not effective in all patients, and produce adverse side effects.

Hormone replacement treatments, used primarily to prevent osteoporosis in menopausal women, enable the risk of fracture to be reduced by only 50%. Moreover, their efficacy in preventing femoral neck fractures has not been established.

The bisphosphonates currently used in the treatment of osteolytic diseases target the prenylation of all of the small G proteins, which are expressed in all cells. The side effects of bisphosphonates are in particular responsible for a large proportion of patients stopping treatment: 50% after one year. Bisphosphonates are toxic for the kidneys, produce gastrointestinal ulcers and the cases of osteonecrosis of the jaw caused by bisphosphonates are constantly increasing.

There is still very little data on Prolia® (Denosumab), but it induces osteonecrosis of the jaw with the same frequency as bisphosphonates, undoubtedly due to the cessation of bone remodeling. Given that Prolia® is a monoclonal antibody, the problems of production methods and costs also arise.

One of the major problems associated with the available treatments (bisphosphonates and Denosumab) is that they completely suppress the osteoclasts by inducing their apoptosis or by preventing their differentiation, which suppresses the stimulant effect of the osteoclasts on the osteoblasts, the cells that produce bone. This leads to a complete cessation of bone remodeling and to weakening of the skeleton.

Since diseases of bone loss are associated with increased activity of osteoclast, it is important to understand the mechanisms by which osteoclasts are activated in these disease states, and to devise rational and therapeutic means to inhibit or reduce this activation.

The disruption in osteoclast adhesion was recently shown to be a beneficial approach to the development of new drugs against excessive bone resorption. The Inventors characterized a new essential actor in this mechanism: the Dock5 protein and Dock5-inhibiting compounds capable of preventing pathological bone resorption in the mouse. Preferably, said DOCK5 protein presents the sequence SEQ ID NO:1 corresponding to the *Mus musculus* sequence of DOCK5.

Dock5 has a tissue expression profile primarily limited to osteoclasts (OCs).

The risk of side effects of specific Dock5 inhibitors is therefore reduced. In addition, there are contraindications to bisphosphonates that may partly be counteracted by this new treatment.

DESCRIPTION OF THE INVENTION

The inventors have presently identified that the DOCK5 protein is implicated in sealing zone formation and consequently in bone resorption. Thus, DOCK5 corresponds to a new therapeutic target for treating and/or preventing bone loss diseases. Finally, the inventors have identified new molecules of general formula I, which permit to inhibit DOCK5 and thus which can be useful for treating and/or preventing bone loss diseases.

According to a first aspect, the present invention is relative to a method for treating and/or preventing a disease in a subject, comprising the step of administrating an effective amount of a compound of formula I to said subject.

The compound of the present invention presents the following formula I:

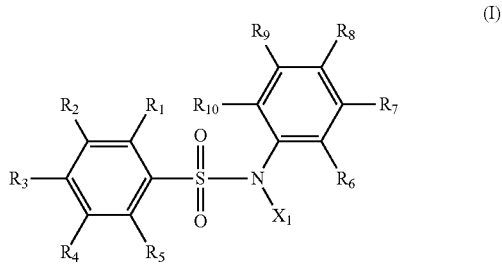

wherein
R1, R2, R3, R4, R5, independently represents an hydrogen or an halogen atom or an alkyl, hydroxyl or alkoxy group, which can be linear or branched and/or unsaturated and optionally substituted, R6, R7, R8, R9 and R10, independently represents a hydrogen, or halogen atom or an alkyl, hydroxyl, amino, nitro, azido, cyano, or alkoxy group, which can be linear or branched and/or unsaturated and optionally substituted, X1 represents an hydrogen or an alkyl group, which can be linear or branched and/or unsaturated and optionally substituted, preferably an hydrogen, or pharmaceutically acceptable salts thereof.

In the meaning of the present invention, "halogen atom" means the group comprising F, Cl, Br and I, preferably said halogen atom is a chlorine atom.

Preferably, at least one of R6, R7, R8, R9 and R10 represents an halogen, advantageously a chlorine atom.

More preferably, at least two of R6, R7, R8, R9 and R10 represent an halogen, advantageously a chlorine atom, and even more preferably two of R6, R7, R8, R9 and R10 represent an halogen.

Preferably, both R7 and R9 represent an halogen, advantageously a chlorine atom.

More preferably both R7 and R9 represent an halogen, advantageously a chlorine atom, and R1, R2, R3, R4, R5, R6, R8, and R10 represent an hydrogen atom.

Preferably X1 is an hydrogen atom.

In a particularly preferred embodiment, the compound of formula I is N-(3,5-dichloro phenyl)benzenesulfonamide or a salt thereof.

N-(3,5-dichloro phenyl)benzenesulfonamide presents the following formula:

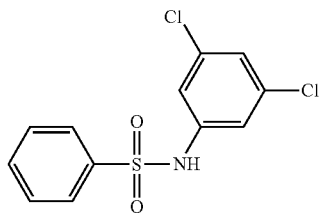 [SMILES: O=S(=O)(Nc1cc(Cl)cc(Cl)c1)c1ccccc1]

The present invention is also relative to a compound of formula I, preferably of N-(3,5-dichloro phenyl)benzenesulfonamide, for its use as a medicament.

More particularly, the compound of formula I, preferably N-(3,5-dichloro phenyl)benzenesulfonamide, is useful for treating disease associated with bone loss.

Consequently, the present invention is also relative to a method for treating and/or preventing a disease associated with bone loss in a subject, comprising the step of administrating an effective amount of a compound of formula I to said subject.

Preferably, said disease associated with bone loss is selected in the group consisting of: menopause, osteoporosis, osteopenia due to bone metastases, inflammatory arthritis, particularly rheumatoid arthritis, more particularly periarticular erosions in rheumatoid arthritis, primary hyperparathyroidism, hypercalcemia of malignancy, Paget's disease of bone, periodontal disease, immobilization induced osteopenia and bone metastasis, particularly bone metastasis associated with breast cancer. More preferably, said disease is osteoporosis.

In particular, bone metastasis is associated with cancer, more particularly with a cancer selected in the group consisting of: breast cancer, prostate cancer, lung cancer, colon cancer, stomach cancer and multiple myeloma.

The present invention is also relative to a compound of formula I for its use as a medicament for the prevention or the treatment of a pathology chosen in the group consisting of: menopause, osteoporosis, osteopenia due to bone metastases, inflammatory arthritis, particularly rheumatoid arthritis, more particularly periarticular erosions in rheumatoid arthritis, primary hyperparathyroidism, hypercalcemia of malignancy, Paget's disease of bone, periodontal disease, immobilization induced ostcopenia and bone metastasis, particularly bone metastasis associated with breast cancer, more preferably, osteoporosis.

In a particular embodiment, said subject is under a glucocorticoid treatment.

In a particular embodiment, said subject is under a postmenopausal woman.

In a particular embodiment, said subject has bone metastases.

Another object of the present invention is relative to a pharmaceutical composition comprising a compound of formula I, preferably N-(3,5-dichloro phenyl)benzenesulfonamide and, optionally, a pharmaceutically acceptable support.

As examples of pharmaceutically acceptable supports, the composition can include emulsions, microemulsions, oil in water emulsions, anhydrous lipids and water in oil emulsions or other types of emulsions.

The inventive composition can further include one or more additives such as diluents, excipients, stabilizers and preservatives. Such additives are well known to those skilled in the art and are described notably in "*Ullmann's Encyclopedia of Industrial Chemistry, 6$^{th}$ Ed.*" (various editors, 1989-1998, Marcel Dekker) and in "*Pharmaceutical Dosage Forms and Drug Delivery Systems*" (ANSEL et al., 1994, WILLIAMS & WILKINS).

Another object of the present invention is relative to a pharmaceutical composition comprising a compound of formula I, preferably N-(3,5-dichloro phenyl)benzenesulfonamide and, optionally, a pharmaceutically acceptable support for treating and/or preventing a disease in a subject in need thereof.

Another object of the present invention is relative to a pharmaceutical composition comprising a compound of formula I, preferably N-(3,5-dichloro phenyl)benzenesulfonamide and, optionally, a pharmaceutically acceptable support for treating and/or preventing bone loss diseases in a subject in need thereof.

As used in the present application, the term "subject" refers to a mammal such as a rodent, cat, dog, primate or human, preferably said subject is a human.

Another object of the invention relates to a therapeutic method for treating and/or preventing bone loss diseases in a subject, comprising the administration of an effective amount of a pharmaceutical composition as described above.

In the meaning of the present invention, an "effective amount" means a quantity that inhibits or reduces the bone resorbing activity of osteoclasts. Those skilled in the art will be able to determine said therapeutically effective quantity based on their general knowledge and on the methods described in the examples.

The compounds can be administered by any mode of administration such as, for example, by intramuscular, intravenous or oral route, etc.

The inventive compounds preferably will be administered at a concentration chosen by those skilled in the art according to the state of advancement of the disease and the targeting mode used, the age and the weight of the subject.

Preferably, the compound will be administered at a concentration of between 2 mg/D/kg and 50 mg/D/kg, preferably at a concentration comprised between 5 mg/D/kg and 30 mg/D/kg.

DESCRIPTION OF THE FIGURES

(FIG. 1A) Total RNA of BMMs induced for differentiation in the presence of RANKL and M-CSF was extracted at days 0, 1, 2, 3 and 4 and levels of Dock5 and Cathepsin K (CtsK) mRNAs relative to Gapdh mRNA were determined by RT-PCR. (FIGS. 1B-1C) Total cell extracts were prepared from FIG. 1B, BMMs treated as FIGS. 1A-1C from RAW264.7 cells grown for the indicated time in the presence of RANKL. Dock5 protein expression was visualized by western blot. (FIG. 1D) Alignment of the aminoacid sequences of the DHR2 exchange domains of mouse Dock5 and Dock1. Black background highlights residues conserved between the two sequences. (FIG. 1E) Total cell extracts were prepared from 293T cells expressing GFP-fused Dock5-DHR2 or GFP and submitted to GTP-trapping using the GST-fused CRIB domain of PAK1. Pulldeddown and total Rac1 and Cdc42 (left panel) and GFP-fusion proteins in total cell extracts (right panel) were revealed by western blot. (FIG. 1F) Localization of GFP-tagged full length Dock5 (green) expressed in RAW264.7-derived OCs was visualized by fluorescence microscopy after staining for vinculin (red) and F-actin (blue) to reveal the podosome belt. Last panel is an enlarged view of boxed areas where yellow color reveals colocalization of Dock5 and vinculin. Scale bar 20 µm.

FIGS. 2A-2F: Dock5 is necessary for bone resorption by OCs derived from BMMs. (FIG. 2A) OCs were differentiated from Dock5+/+ (+/+) and Dock5-/- (-/-) BMMs and stained for TRAP activity. Scale bars 200 µm. (FIG. 2B) OCs were differentiated on Osteologic Biocoat from Dock5+/+ and Dock5-/- BMMs and stained for actin to reveal the sealing zones (arrows). Insets show enlarged boxed areas. Scale bars 100 µm. (FIG. 2C) Proportion of OCs obtained as in FIG. 2B with a sealing zone. Graph shows average and SD of three independent OC preparations counting over 300 cells. a: p<0.001, Mann-Whitney test. (FIG. 2D) Scanning electron micrographs showing OCs differentiated on bone slices. Arrows point at resorption pits. (FIG. 2E) Bone slices from FIG. 2D were stained with WGA lectin to reveal resorption pits (Arrows). (FIG. 2F) CTx concentrations measured in the culture medium of OCs grown on bone slices as in FIGS. 2D-2E. Graph shows average and SD CTx concentration per OC relative to Dock5+/+ control OC from three independent experiments performed in triplicate. a: p<0.001, Mann-Whitney test.

FIGS. 3A-3E: Dock5 is dispensable for the expression of OC characteristic genes and for Rac1 activation in response to M-CSF and adhesion. (FIGS. 3A-3B) Total RNAs were prepared from Dock5+/+ (+/+) and Dock5-/- (-/-) BMMs gown for 5 days in the presence of M-CSF (black bars) or of RANKL and M-CSF (white bars). mRNAs levels of OC characteristic genes (FIG. 3A) and from Dock1 and Dock2 (FIG. 3B) relative to Gapdh were determined by RT-PCR. (FIG. 3C) Rac1 activity was measured by G-LISA in Dock5+/+ and Dock5-/- OCs at day 4 of differentiation stimulated with 100 ng/ml M-CSF for the indicated amount of time. (FIG. 3D) The levels of total and phosphorylated ERK1/2 were determined by western blot in Dock5+/+ and Dock5-/- OCs stimulated with M-CSF as in FIG. 3C. (FIG. 3E) Rac1 activity was measured by G-LISA in Dock5+/+ and Dock5-/- OCs at day 4 of differentiation lifted and left in suspension (s) or replated onto vitronectin coated plates for 30 minutes (a). FIG. 3C and FIG. 3E show average active Rac1 and SD of duplicate measures in one experiment representative of two independent OC preparations.

FIGS. 4A-4I: Dock5 deficient OCs have less active Rac1 and adhesion defects and reduced p130Cas phosphorylation. (FIG. 4A) Western blot showing total and GTP-bound Rac1 in extracts of Dock5-/- and Dock5+/+ OCs. FIG. 4B Western blots showing total and GTP-bound Rac1 (left panel) and Dock5 and Gapdh (right panel) in extracts of RAW264.7-derived OCs expressing Dock5 (shDock5) or control (shLuc) shRNAs. Figures in FIGS. 4A and 4B show average and SD active Rac1 levels in Dock5 deficient OCs relative to controls in two independent experiments, western blots show one experiment. (FIG. 4C) Dock5+/+ and Dock5-/- OCs were stained for TRAP to reveal global cell shape. Scale bars 200 µm. FIG. 4D OC average and SD circularity from four independent OC preparations measuring at least 60 OCs from 4 independent microscope fields in each experiment. a: p<0.001, Mann-Whitney test. FIG. 4E OCs remaining bound after 5 minutes incubation with the indicated concentration of EDTA, determined by crystal violet staining. Graph represents average and SD of two independent experiments performed in triplicates. b: p<0.01, n.s.: non significant change, Mann-Whitney test. (FIG. 4F) Western blot revealing global tyrosine phosphorylation with 4G10 antibody in OC lysates. (FIG. 4G) Western blots showing p130Cas (Cas), Pyk2 and Crk in control (-) or 4G10 immunoprecipitates (IP) and in total lysates (TCL). (FIG. 4H) Average and SD levels of p130Cas (Cas), Pyk2 and Crk phosphorylation in OCs from two independent experiments, one is shown in (FIG. 4G). a: p<0.001, n.s.: non significant change, Mann-Whitney test. (FIG. 4I) Western blot showing phosphorylated p130Cas (PCas) revealed by 4G10 and total p130Cas (Cas) in p130Cas immunoprecipitates of OC lysates. (FIG. 4J) Quantification of phosphorylated versus total p130Cas in the experiment shown in FIG. 4I.

FIGS. 5A-5H: Inhibition of bone resorption by an inhibitor of Rac1 activation by Dock5. (FIG. 5A) Principle of the yeast exchange assay used to identify inhibitors of Dock5 exchange activity. Wild type Rac1 is fused to LexA DNA binding domain (LexA) and its effector Kinectin (Kin) to GAL4 activation domain (GAD). Expression of Dock5-DHR2 activates Rac1, which binds to kinectin, leading to the expression of his3 and then yeast auxotrophy for histidine. Inhibitors of Dock5-DHR2 revert Rac1 activation. (FIG. 5B) Growth curves of yeasts expressing Rac1 and Kinectin with (open triangles) and without (dots) Dock5-DHR2, in medium complemented (plain lines) or not (dotted lines) with histidine. (FIG. 5C) Structure of N-(3,5-dichlorophenyl)benzensulfonamide (C21). (FIG. 5D) Western blots showing total and GTPbound Rac1 (upper panels) and GFP and GFP-fused Dock5-DHR2 in extracts of 293T cells treated for 1 hour with the indicated concentrations of C21 in the presence of 1% DMSO. (FIG. 5E) Western blots showing total and GTP-bound Rac1 (upper panels) and GFP and GFP-fused TrioN in extracts of 293T cells treated as in FIG. 5D. (FIG. 5F) Number of OCs (OC) after a 24-hour incubation with the indicated concentrations of C21, expressed as a % of DMSO control (0 µM C21). Graph shows average and SD of two to three independent experiments performed in triplicates. (FIG. 5G) CTx concentration in the medium of OCs on bone in the absence (O) or presence of 25 µM C21. Graph shows average and SD of three experiments performed in duplicates with independent OC preparations. a: p<0.001, Mann-Whitney test. (FIG. 5H) CTx production per OC in the presence of the indicated concentration of C21. Graph shows average and SD CTx concentration per OC in one experiment performed in triplicates.

FIGS. 6A-6G: Suppression of Dock5 leads to reduced trabecular bone mass in mice. (FIG. 6A) Levels of Dock5 mRNA relative to Gapdh mRNA determined by RT-PCR in BMMs grown with M-CSF (ND) or differentiated into OCs for 5 days (D5) and in proliferating MSCs and MSC-derived osteoblasts (OB) (FIG. 6B) mRNA levels of the indicated osteoblast differentiation marker genes relative to Gapdh in proliferating MSCs and osteoblasts from FIG. 6A and mineralization activity of the osteoblasts revealed by Alizarin Red S staining. (FIG. 6C) Total proteins extracted from BMMs grown with M-CSF (ND) or for 3 and 5 days with M-CSF and RANKL and from various mouse tissues (Ey: Eye, Sp: Spleen, St: Stomach, Te: Testis, Pl: Placenta, Lu: Lung, Br: Brain, He: Heart, Li: Liver, Ki: Kidney; Mu: Muscle) were analyzed by western blot with antibodies against Dock5 and against tubulin for normalization. (FIG. 6D) Percent bone volume/total volume (BV/TV) in distal femur of 7-week-old mice (n=6). a: $p<0.001$, Mann-Whitney test. (FIG. 6E) Histological section showing distal femur of 7-week-old mice stained with von Kossa to reveal mineralized tissue. (FIG. 6F) OC number per bone perimeter (OC/mm) in distal femur of 7-week-old mice (n=6). (FIG. 6G) Histological sections from distal femur of 7-week-old mice stained for TRAP activity to visualize OCs and counterstained with hematoxylin to visualize bone trabeculae.

(FIG. 7A) At the end of a resorption phase, the sealing zone disassembles (dotted thick black line) around the newly formed resorption pit (dashed area). (FIG. 7B) Under the stimulation of M-CSF, Vav3 gets activated and in turn activates Rac1 downstream of c-Fms, allowing the OC to spread away from its previous resorption pits (arrows) and the initiation of a new sealing zone (thick black circle). (FIG. 7C) Then the stable interaction of c-Fms with □vβ3 promotes the assembly of the p130Cas-CrkII signaling scaffold to sustain robust activation of Rac1 by Dock5, allowing the enlargement and stabilization of the sealing zone (arrows) for an efficient new bone resorption step (FIG. 7D).

EXAMPLES

Figures 1A, 1B:
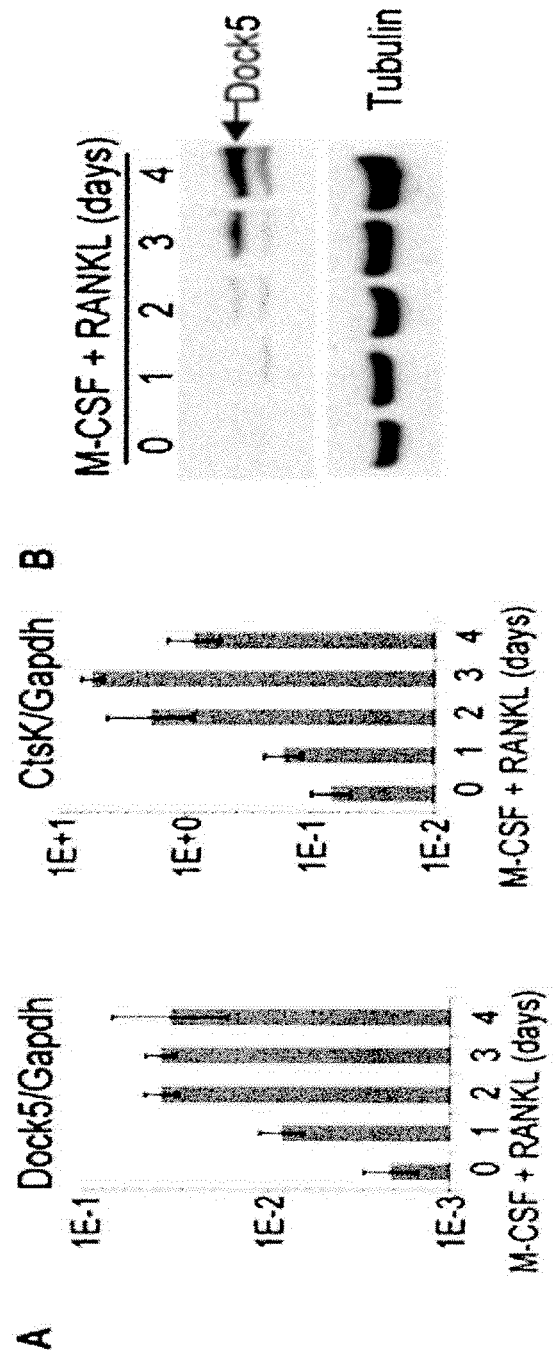
FIGS. 1A-1F: Dock5 is a Rac1 exchange factor expressed in osteoclasts (OCs).

I. The Rac1 Exchange Factor Dock5 is Essential for Bone Resorption by Osteoclasts Materials and Methods Mice.

Dock5-/- mice were previously described (14). Mice used were 4 to 8-week-old and were maintained at the animal facilities of the CNRS in Montpellier.

Histological Analyses.

Femurs of 8-week old mice were fixed for one week in 10% formalin in PBS, embedded in Historesin (Leica), 7 µm sections stained with von Kossa and counterstained with von Gieson.

Alternately, bones were decalcified in 10% EDTA for 10 days, embedded in paraffin and 4.5 µm sections stained for TRAP activity and counterstained with a nuclear fast red. Measures were done in a standard zone in distal femur situated 250 µm from the growth plate excluding the primary spongiosa. Bone volume, total volume, OC numbers and bone perimeters were measured in the same region of interest on three adjacent slides, using Bioquant OSTEO II (Bioquant Image Analysis).

Production of OCs and Osteoblasts.

BMMs were isolated from long bones of 4- to 8-week-old animals as described (16) and OCs obtained by culturing BMMs with RANKL (100 ng/ml) and M-CSF (10 ng/ml) (Peprotech) for 5 days. RAW264.7 cells were grown for 5 days with RANKL (50 ng/ml) to obtain OCs. For resorption, OCs were differentiated in multiwell chambers or on coverslips coated with calcium phosphate (Osteologic Biocoat, BD Bioscience) or in 96-well plates containing a bovine bone slice (IDS Nordic Bioscience). Mesenchymal stem cells (MSCs) were isolated from mouse bone marrow and grown as described (18).

Osteogenesis was induced by culture at low density (3×10$^4$ cells in 6-well plates) for 21 days in osteogenic medium (DMEM supplemented with 10% FBS, 2 mM glutamine and 0.05 mM ascorbic acid), supplemented with 3 mM NaH2PO4 for mineralization assays. Osteoblasts were characterized by alizarin red S staining of the secreted calcified extracellular matrix as previously described (18).

Microscopy, Immunofluorescence and TRAP Labeling.

OCs were fixed and stained for DNA, actin or vinculin or TRAP as described (16,19). Antivinculin antibody (Sigma) was revealed with Alexa Fluor 546-conjugated secondary antibody and actin stained with Alexa Fluor 360 or 488-conjugated phalloidin (Invitrogen).

Preparations were mounted in Mowiol 40-88 (Sigma) and imaged with Zeiss Axioimager Z2 microscope with Coolsnap HQ2 camera for fluorescence and Coolsnap color Cf camera using Zeiss 40× PLAN-NEOFLUAR 1.3 oil DIC or Zeiss 20× PLAN-APOCHROMAT 0.8 or Zeiss 10× EC PLAN-NEOF- LUAR 0.3. Images were acquired with MetaMorph 7.0 software (Molecular Devices). OC circularity was measured using ImageJ. OCs were counted manually in 96-well plates stained to reveal DNA and TRAP activity, except in FIG. 5F where they were counted automatically using a Cellomics Arrayscan VTI (Thermo Scientific). For scanning electron microscopy, OCs on bone slices were fixed in PBS containing 3% glutaraldehyde and post-fixed with 1% OsO4. After alcohol dehydration, OCs were dried in hexamethyldisilazane (Acros Organics, NJ, USA) for 2 min, coated with Goldpalladium and observed using a Hitachi S4000 scanning microscope at 10 kV.

Adhesion Assays.

OCs differentiated in 96-well plates were incubated for 5 minutes in PBS supplemented or not with 0.25 mM EDTA. Wells were then rinsed with PBS, fixed, stained with 0.1% crystal violet, lysed and OD595 was measured as described (19). Each condition was performed in triplicate wells.

Plasmid DNAs.

Yeast expression vectors for Rac1 and Kinectin (20,21) and GFP-fused TrioN (22) were reported previously. The obtain full length Dock5 cDNA, BamH1-Kpn1 fragment of RIKEN clone E130320D18 (nucleotides 249 to 1,913 of Dock5 mRNA), was fused to the Kpn1-Not1 fragment of IMAGE clone 30106676 (nucleotides 1,914 to 6,461 of Dock5 mRNA). The whole was fused to GFP and was inserted into pMXs-puro (23), a gift from Dr Kitamura, Tokyo, Japan. Dock5 DHR2 domain (aminoacids E1119 to L1667) was cloned into pEGFP (Clontech) or myc tagged in pRs426Met (21). Dock5 and firefly luciferase shRNA expression vectors were described previously (BRAZIER et al, *Expression profile of RhoGTPases and RhoGEFs during RANKL-stimulated osteoclastogenesis: identification of essential genes in osteoclasts,* 2006, J Bone Miner Res 21(9):1387-98.) as well as methods to produce and use retroviruses (BRAZIER et al, *The Rho GTPase Wrch1 regulates osteoclast precursor adhesion and migration,* 2009, Int J Biochem Cell Biol 41(6): 1391-401.).

RT-PCR and Primers.

RT-PCR analyses were performed as described (BRAZIER et al, 2009, see above). Amplification primers were:

```
                                           (SEQ ID NO: 2)
5'-GGCTGTGTTTACCGACGAGC-3'
and
                                           (SEQ ID NO: 3)
5'-CAAGCACGCGGACAATGTTG-3'
for Calcitonin receptor, (SEQ ID NO: 4)
5'-TCAGCTTCAGCATTCAGCCC-3'
and
                                           (SEQ ID NO: 5)
5'-ACTGCACGATTCCAGAGTCC-3'
for Dock1 and (SEQ ID NO: 6)
5'-AGCCTTGCATCTCCTGTGGC-3'
and
                                           (SEQ ID NO: 7)
5'-CATGCGTCCCTTGGATGCTG-3'
for Dock2, (SEQ ID NO: 8)
5'-GCG CTC TGT CTC TCT GACCT-3'
and
                                           (SEQ ID NO: 9)
5'-GCC GGA GTC TGT TCA CTA CC-3'
for Osteocalcin,
```

```
                                          (SEQ ID NO: 10)
5'-AAT GCC CTGAAA CTC CAA AA-3'
and
                                          (SEQ ID NO: 11)
5'-AGG GGA ATT TGT CCA TCT CC-3'
for Alkaline Phosphatase, (SEQ ID NO: 12)
5'-TGT TCA GCT TTG TGG ACC TC-3'
and
                                          (SEQ ID NO: 13)
5'-TCA AGC ATA CCT CGGGTT TC-3'
for Collagen I.
```

Other primers were described: Gapdh, Dock5, Vav3, Src, TRAP, NFATc1, CtsK, Integrin β3, DC-STAMP and ATP6v0d2 (BRAZIER et al, 2006 and BRAZIER et al, 2009, sec above), OSCAR, CD44 (KIM et al *NFATc1 Induces Osteoclast Fusion Via Up-Regulation of Atp6v0d2 and the Dendritic Cell-Specific Transmembrane Protein (DC-STAMP),* 2008, Mol Endocrinol 22(1):176-85) and ADAM8 (CHOi et al. *ADAM8: a novel osteoclast stimulating factor,* 2001 J Bone Miner Res 16(5):814-22.

Active Rac1 Quantification.

GTP-bound Rac1 was pulled down from OC or 293T cell extracts using GST-fused PAK1 CRIB domain as described (BOUQUIER et al., *A cell active chemical GEF inhibitor selectively targets the Trio/RhoG/Rac1 signaling pathway,* 2009, Chem Biol 16(6):657-66.) and revealed by western blot with monoclonal anti-Rac1 antibodies (Transduction Laboratories) and anti-GFP polyclonal antibodies (Torrey Pines Biolabs). To activate Rac1, OCs at day 4 of differentiation were starved overnight in the presence of 2% serum, stimulated with 100 ng/ml M-CSF or lifted and replated onto vitronectin-coated plates for 30 minutes prior to lysis, and active Rac1 levels were measured G-LISA kit according to manufacturer's instructions (Cytoskeleton).

Immunoprecipitation, Western Blot and Antibodies.

Antibodies for phosphorylated Erk-1/2 were from Cell Signaling and for total Erk1/2 from Santa Cruz. Antibodies for Crk, p130Cas and Pyk2 antibodies were from Transduction Laboratories. 4G10 phosphotyrosine specific antibodies were a gift from Dr Bettache, Montpellier, France. OC were lysed in lysis buffer (50 mM Tris pH 7.5, 120 mM NaCl, 1 mM EDTA, 6 mM EGTA, 1% NP-40, 20 mM NaF, 100 μM Na3VO4) and directly analyzed by western blot for total tyrosine phosphorylation analysis. For immunoprecipitation, precleared lysates were precipitated and analyzed by western blot with the appropriate antibodies.

Immunocomplexes were visualized by the ECL Western Lightning Plus detection system (Perkin Elmer) with horseradish peroxidase-conjugated secondary antibodies (GE Healthcare) and quantified using ImageJ.

Resorption Assays.

OCs in multiwell Osteologic Biocoat were fixed at day 7 of differentiation and calciumphosphate was stained with von Kossa as described (BRAZIER et al, 2009, see above). The entire well surface was imaged using a Zeiss AxioimagerZ1 microscope. Well image was reconstituted and resorbed areas were measured using MetaMorph 7.0 software (Molecular Devices). For bone resorption assays, OCs were derived from BMMs in 96-well plates containing bovine bone slices. At day 5 of differentiation, medium was changed with fresh medium. After 2 days, CTx concentrations were measured using Crosslap (IDS Nordic Bioscience). To reveal resorption pits, bone slices were incubated for 1 hour in peroxidase conjugated wheat-germ agglutinin (WGA) lectin (SIGMA)

in PBS (20 μg/ml) followed by detection of peroxidase activity using SIGMAFAST according to manufacturer's instructions (SIGMA).

Yeast Methods.

Screening for Dock5 inhibitors was performed in TAT7 yeast disrupted for erg6 essentially as described for the RhoGEF TrioN (20,21). Briefly, yeasts were grown in 96-well plates in histidine free and histidine complemented drop out medium supplemented with 1% DMSO and 100 μM of one of the 2,640 chemical compounds to be tested (ChemBridge™, San Diego, Calif.) (ANDRE et al., *A multiwell assay to isolate compounds inhibiting the assembly of the prokaryotic RNA polymerase*, 2004, Assay Drug Dev Technol 2(6):629-35). Growth curves were established by measuring OD600. Inhibitors were selected for their ability to inhibit selectively growth acceleration in histidine-free medium conferred by Dock5-DHR2 expression without affecting growth in histidine-supplemented medium.

Statistical Analyses.

Statistical significances were determined using Mann-Whitney non-parametrical test.

Results.

Dock5 is a Rac1 GEF associated with OC adhesion structures.

Figures 1C, 1D:
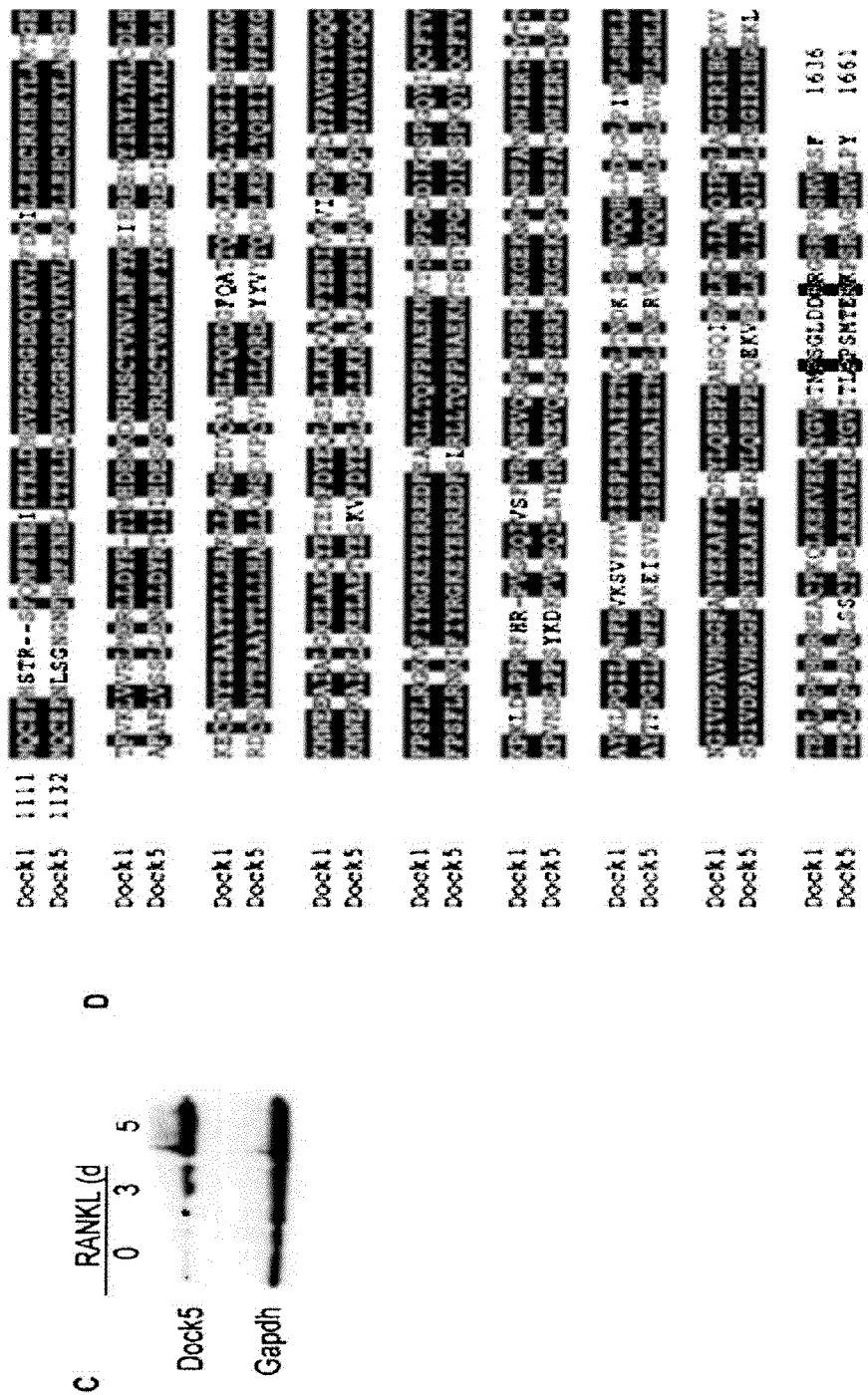
Figure 1E:
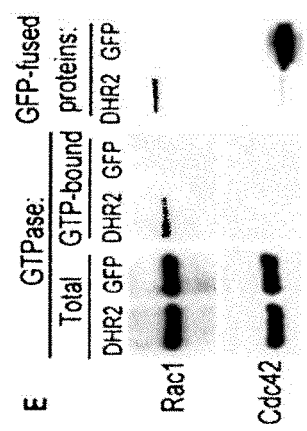
Figure 1F:
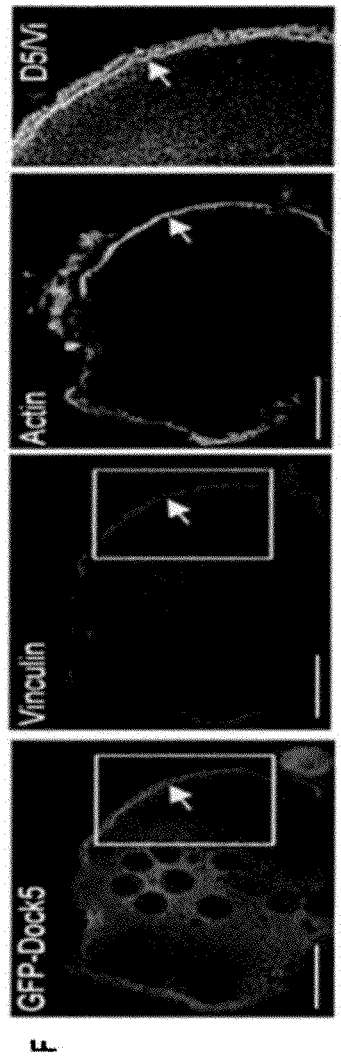

The inventors previously identified Dock5 as a RhoGEF gene strongly induced during RANKL stimulated osteoclastogenesis in RAW264.7 cells and BMMs (FIG. 1A). Purified antibodies directed against the C-terminal end of Dock5 confirmed the great increase of Dock5 expression during osteoclastic differentiation of BMMs (FIG. 1B) and RAW264.7 cells (FIG. 1C). Previous in vitro observations suggested that Dock5 could activate the GTPase Rac1. To confirm this on endogenous Rac1,
the DHR2 domain of mouse Dock5, lying between aminoacids M1132 and Y1661 and
corresponding to the equivalent domain defined in Dock1 was expressed in HEK-293T cells (FIG. 1D). Pull down assays, using the GTPase binding domain of the kinase PAK1 that selectively binds to active Rac1 and Cdc42, showed that Dock5 can activate endogenous Rac1 without affecting Cdc42 activity (FIG. 1E, left panel). Expression of GFP fusion proteins was assessed by western blot (FIG. 1E, right panel). GFP-tagged full length Dock5 expressed in RAW264.7 cell-derived OCs colocalizes with vinculin at the podosome belt (FIG. 1F).

Dock5 is Essential for OC Function In Vitro.

To investigate the role of Dock5 in OC biology, we downregulated Dock5 in RAW264.7 cells using shRNAs. Whereas complete silencing of Dock5 leads to massive detachment of cells around day 3 of differentiation, lower retroviral concentrations leading to moderate silencing of Dock5 protein (FIG. S1A) allows efficient formation of TRAP positive multinucleated cells in response to RANKL (FIG. S1B). Strikingly, these OCs seeded on calcium-phosphate-coated substrates do not form sealing zones (FIG. S1C). Accordingly, they do not resorb the mineral substrate (FIG. S1D). Consistently, OCs derived from shDock5-expressing BMMs exhibit very few and small sealing zones (FIG. S1E) and have reduced bone resorbing activity (FIG. S1F). This suggests that Dock5 is involved in formation of the sealing zone and then, in bone resorption by OCs. To further study the physiological role of Dock5 in OCs, OCs from primary BMMs isolated from Dock5+/+ and Dock5-/- mice were differentiated. Dock5-/- BMMs differentiate into OCs defined as TRAP positive multinucleated cells (FIG. 2A). But Dock5-/- OCs fail to assemble sealing zones when seeded on calcium-phosphate substrates (FIG. 2B-C) and they do not resorb the calcium-phosphate mineral substrate (not shown). Electron micrograph of bone slices seeded with Dock5-/- OCs showed that they can adhere on bone, but they were never found associated with a resorption pit (FIG. 2D). Staining with WGA lectin showed that bone slices seeded with Dock5-/- OCs have very few and small resorption pits (FIG. 2E). Measurement of degradation products of C-terminal telopeptide of type I collagen (CTx) production in the culture medium indeed confirmed that Dock5-/- OCs are defective for bone resorption (FIG. 2F). These results characterize Dock5 as being essential for the formation of OC sealing zone and subsequent bone resorption.

Dock5 is Necessary for Rac1 and p130Cas Activation in OCs.

The importance of Dock5 for RANKL induced expression of osteoclastic marker genes exploiting Dock5+/+ and Dock5-/- BMMs was next evaluated. Real-time Q-PCR did not reveal any defect in the expression of the 12 genes tested (FIG. 3A). In particular, ITGB3, Src and Vav3 that are involved in sealing zone formation are expressed at normal levels. We also noticed that Dock5 deficiency does not induce a compensatory overexpression of Dock1 or Dock2, the closest Dock5 paralogs (FIG. 3B). Thus, suppression of Dock5 does not appear to prevent the establishment of the OC specific transcriptional program.

It was then investigated how the absence of Dock5 may impact on the activation of Rac1 in OCs. M-CSF regulates OC cytoskeleton and induces rapid activation of Rac1 leading to the phosphorylation of Erk1/2. Integrin αvβ3 stimulation by adhesion of OC onto vitronectin also activates Rac1. In the absence of Dock5, we found that M-CSF induces normal Rac1 activation and Erk1/2 phosphorylation (FIG. 3C-D) and adhesion stimulated activation of Rac1 is not affected (FIG. 3E). It was then looked at the steady state level of Rac1 activity in adherent OCs under no stimulation. In this case, active Rac1 pull down assays showed a strong reduction in Rac1 activity in OCs derived from Dock5-/- BMMs or from RAW264.7 cells expressing Dock5 shRNAs (FIG. 4A-B). Dock5-/- OCs exhibited very irregular shapes on plastic (FIG. 4C) as confirmed by significantly reduced circularity (FIG. 4D). Furthermore, Dock5-/- OCs are less resistant to detachment from the substrate upon EDTA treatment (FIG. 4E). These results show that in the absence of Dock5, OCs have low levels of Rac1 activity associated with spreading and adhesion defects.

It was next investigated candidate signaling molecules known to participate in the control of OC adhesion that could be linked to Dock5 and Rac1 signaling. The adaptor protein p130Cas is involved in actin organization in OCs. Dock1 is known to stimulate signaling from the CrkII-p130Cas complex by increasing p130Cas tyrosine phosphorylation, which in turn stimulates Rac1 activation by the GEF. Dock5 was shown to control epithelial cell spreading through its binding to CrkII. The overall tyrosine phosphorylation profile in adherent OCs was not modified in the absence of Dock5 (FIG. 4F) but we found less p130Cas in phosphotyrosine specific immunoprecipitates of Dock5-/-OC lysates (FIG. 4GH). Consistently, low levels of tyrosine phosphorylated p130Cas were found in Dock5-/-OC extracts immunoprecipitated with p130Cas specific antibodies (FIG. 4I-J). It was also observed increased CrkII phosphorylation (FIG. 4G-H), which is known to prevent binding of CrkII to p130Cas. Conversely, phosphorylation of Pyk2, a partner of p130Cas in OCs involved in sealing zone formation, remained unchanged in the absence of Dock5 (FIG. 4G-H). Taken together, these results suggest that the absence of Dock5 in OCs leads to adhesion defects associated with defective activation of Rac1 and p130Cas.

A Chemical Inhibitor of Rac1 Activation by Dock5 Hinders OC Bone Resorbing Activity.

To confirm the essential role of Rac1 activation by Dock5 in the resorption process, it was sought for a chemical inhibitor of Dock5 exchange activity active in cell cultures. The inventors therefore took advantage of a yeast-based assay that they have developed (BLANGY et al., *Identification of TRIO-GEFD1 chemical inhibitors using the yeast exchange assay,* 2006, Biol Cell 98(9):511-22 and BOUQUIER et al. *A cell active chemical GEF inhibitor selectively targets the Trio/RhoG/Rac1 signaling pathway,* 2009, Chem Biol 16(6):657-66.). They constructed a yeast strain where Rac1 activation by Dock5 DHR2 induces the expression of the his3 reporter gene (FIG. 5A), which leads to faster yeast growth in Histidine deprived medium (FIG. 5B). A library of 2,640 heterocyclic commercial chemical compounds as described previously was screened (BOUQUIER et al., see above) for molecules able to inhibit growth of Dock5 DHR2-expressing yeasts in Histidine deprived medium without affecting growth in Histidine complemented medium. C21: N-(3,5-dichlorophenyl) benzenesulfonamide was then identified (FIG. 5C). C21 efficiently inhibits the activation of Rac1 by Dock5-DHR2 in HEK293T cells (FIG. 5D) but has no effect on Rac1 activation by the GEF TrioN (FIG. 5E). OC survival assays showed that C21 provokes OC death at concentrations above 25 μM (FIG. 5F). 25 μM C21 efficiently inhibits the resorption of calcium-phosphate matrices (not shown) and bone resorption, as assessed by measurement of CTx concentration in the culture medium of OCs (FIG. 5G). In parallel, control OCs grown in the presence of DMSO or 25 μM C21 were stained for TRAP to ascertain C21 was not toxic (not shown). Dose response experiment confirmed that C21 efficiently inhibits bone resorption by OCs in vitro (FIG. 5H). These results show that a small chemical compound preventing Rac1 activation by Dock5 efficiently suppresses bone resorption by OCs in vitro.

Dock5 Deficiency Leads to Increased Trabecular Bone Mass in Mouse.

The tissue distribution of Dock5 in mice was explored. Interestingly, no activation of Dock5 transcription was found in the bone forming mature osteoblasts derived from MSCs (FIG. 6A) while the expression of osteoblast differentiation marker genes showed a very strong increase (FIG. 6B). Western blot analyses of protein extracts from a variety of mouse tissues showed that Dock5 is predominantly expressed in OCs, testis and placenta (FIG. 6C). Although expressed in these latter tissues and in ovary (not shown), Dock5−/− mice breed normally (not shown), suggesting that Dock5 does not play an essential function in mouse reproduction. This shows that the expression of Dock5 is restricted to a very narrow set of tissues in mice, including bone degrading OCs and excluding bone forming osteoblasts.

Quantitative bone histomorphometry performed on histological slices revealed that trabecular bone volume to total volume ratio (BV/TV) is increased over 30% in Dock5−/− mice as compared to wild type animals: 19%±3.5 in Dock5−/− vs 14.3%±2.6 in Dock5+/+ (FIG. 6D-E). In parallel, it was found that OC number per bone surface (OC/mm) is identical in both genotypes: 11.2±3.4° C./mm in Dock5−/− vs 12.5±3.4 Dock5+/+ (FIG. 6F-G).

Together with the in vitro observations, these data are consistent with an essential role of Dock5 for bone resorption but not for differentiation of OCs.

Discussion

Increased bone resorption by OCs is associated with various physiological disorders and pathological situations including hormonal defects, inflammation and cancer. Our study provides evidence that inhibition of Dock5 could be a novel approach to regulate bone loss.

The data highlight the essential role of this atypical Rac1 exchange factor in bone resorption: in the absence of Dock5, OCs differentiate but are unable to resorb bone due to their inability to form a sealing zone. We show that inhibition of Rac1 activation by Dock5 using a small chemical compound can modulate bone resorption. Finally, we found that Dock5−/− mice have increased trabecular bone mass associated with normal number of OCs, showing that Dock5 is also essential for bone resorption in vivo.

Targeting small GTPase signaling pathways using nitrogen containing bisphosphonates (N-BPs) has long proven an efficient strategy to control bone resorption by OCs in a variety of pathological situations. N-BPs inhibit the C-terminal prenylation of small GTPases from the Ras, Rab and Rho families, inducing the accumulation of unprenylated small GTPases and provoking OC dysfunction and death. However, N-BPs target a wide range of small GTPases that control many signaling cascades, which may be a reason for the undesirable side effects arising from N-BPs-based treatments. Considerable effort is currently being made to develop novel antiresorptive agents by targeting processes more specific to OCs such as RANKL antibodies or Cathepsin K inhibitors. It was found that Dock5 is predominantly expressed in OCs; in particular it is not expressed in osteoblasts, the bone forming cells. Furthermore, Dock5−/− mice do not present major phenotypic defects. This suggests that inhibiting Dock5 in vivo could reduce the activity of OCs without affecting bone formation and other physiological functions. Therefore, targeting Dock5 exchange activity could represent a valuable strategy for the development of novel anti-osteoporotic treatments.

The inventors used several experimental approaches to investigate the function of Dock5 in OCs. While all consistently leading to the conclusion that Dock5 is essential for OC bone resorbing activity, the experimental systems used showed minor discrepancies. In particular, it was not observed any toxic effect of Dock5 shRNAs upon differentiating BMMs into OCs, contrarily to what we had observed in RAW264.7 cells. This may reflect high infection efficiency of RAW264.7 cells as compared to BMMs as it was never obtained complete silencing of Dock5 in primary cells. The toxic effect observed in RAW264.7 cells is most likely due to off target effects resulting from high levels of shRNAs rather than complete silencing of Dock5 as differentiation of Dock5−/− BMMs into OCs does not result in cell death.

Rho GTPases are well-established regulators of the actin cytoskeleton, which is highly dynamic in OCs, in particular during the resorption process when podosomes reorganize into a sealing zone. The inventors showed that among the many RhoGEF genes expressed in OCs, only Dock5 and the RhoA GEF Arhgef8 exhibit strong transcriptional activation during RANKL induced osteoclastogenesis. The inventors confirm now that the expression of Dock5 protein is indeed much higher in OC as compared to BMMs. In line with these findings, Ha et al. (*Proteomic profile of osteoclast membrane proteins: identification of Na+/H+ exchanger domain containing 2 and its role in osteoclast fusion,* 2008, Proteomics 8(13):2625-39) reported a quantitative proteomic study showing that after ATP6v0d2, which is critical for OC differentiation, Dock5 is the second most abundant membrane associated protein differentially expressed in OCs as compared to macrophages. The inventor's results did not reveal a role for Dock5 during OC differentiation per se. Dock5−/− mice have a normal number of OCs and Dock5−/− BMMs efficiently differentiate in vitro into OCs that express all characteristic genes tested. Conversely, Rac1 was shown to be necessary for the expression of the OC markers TRAP and Cathepsin K. Therefore, it is likely that GEFs distinct from Dock5 are needed to activate Rac1 for the control of gene expression during OC differentiation. In particular, the exchange factor Vav3 is required for Rac1 activation and expression of late OC differentiation markers Calcitonin receptor, TRAP and Cathepsin K.

Figures 7A, 7B, 7C, 7D:
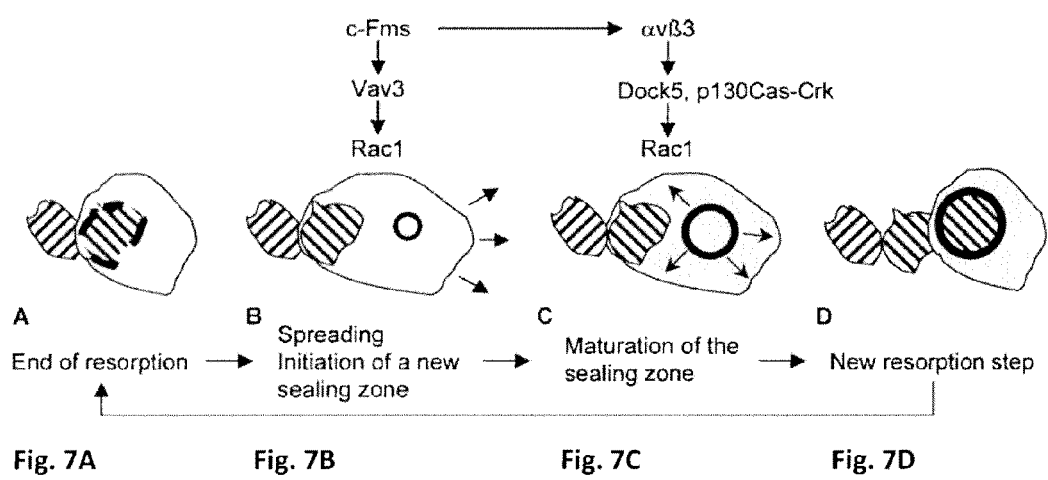
FIGS. 7A-7D: Model for the respective functions of Dock5 and Vav3 during OC resorption cycle. OCs alternate between resorption and spreading phases.

Normal induction of the differentiation program suggests that the defects observed in Dock5−/− OCs result from signaling defects, although it cannot be excluded that important but as yet unidentified genes require Dock5 for their transcriptional activation during differentiation. The inventors found that the steady state activity of Rac1 is reduced in OCs lacking Dock5. Interestingly, they also found reduced phosphorylation of p130Cas in the absence of Dock5. In OCs, M-CSF was shown to induce the stable interaction of c-Fms with $\alpha v\beta 3$ integrin and p130Cas. This leads to the phosphorylation of p130Cas, which is involved in the formation of the sealing zone. Besides, Dock1 was shown to increase p130Cas phosphorylation and to positively regulate signaling from integrins to the p130Cas-Crk signaling complex, which favors Rac1 activation. Altogether, this suggests that Dock5 and p130Cas could be involved in a common signaling network to control the activation of Rac1 in OCs. Vav3 is also required for the formation of the sealing zone (31). Nevertheless, the inventor's findings suggest that the signaling pathways controlled by Dock5 and Vav3 during this process are distinct. Indeed, M-CSF and adhesion stimulated activation of Rac1 requires Vav3 whereas the inventors found that it is independent of Dock5. M-CSF and adhesion were shown to activate Vav3, which is then recruited with Rac1 at the plasma membrane of OCs (49). It was found that Dock5 associates with OC podosome belt. A possible hypothesis would be that Dock5 and Vav3 regulate Rac1 activation at distinct locations in OCs and at different phases of bone resorption cycle (FIG. 7). For efficient resorption, OCs alternate between spreading and resorption steps that involve disassembly and reformation of the sealing zone. After the end of a resorption step, activation of c-Fms by M-CSF and of integrins through adhesion would recruit and activate Vav3 at the plasma membrane, leading to rapid activation of Rac1. This would allow OC spreading and actin remodeling necessary for the initiation of new sealing zone formation (FIG. 7B). Then, stable interaction of c-Fms with $\alpha v\beta 3$ by promoting the assembly of a signaling scaffold involving the p130Cas-CrkII complex would sustain robust activation of Rac1 by Dock5 at the actin ring. This would allow the stabilization of the sealing zone necessary for efficient bone resorption (FIG. 7C).

Dock5−/− mice have increased trabecular bone volume with normal number of OCs. This is in line with our in vitro observations showing that Dock5 is essential for resorption but not for OC differentiation. Although the effect of Dock5 suppression is very drastic for OC activity in vitro, Dock5−/− animals do not show severe bone mass increase. The phenotype of Dock5−/− mice is consistent with the moderate osteopetrotic phenotype reported for mice with targeted deletion of Rac1 in OCs. The moderate phenotype of Dock5−/− mice may be due to adaptive physiological mechanisms that may compensate for the low resorbing activity of OCs in vivo but are not activated in the in vitro model of cultured OCs. In particular, it was not observed increased expression of Vav3, Dock1 or Dock2 in Dock5−/− OCs in culture. These or other Rac1 GEFs expressed in OCs may complement partially Dock5 deficiency in vivo. In line with this hypothesis, it was reported previously that Dock1 and Dock5 are partially redundant during muscle fiber formation. Consistent with the restricted distribution of Dock5, Dock5−/− mice do not present major phenotypic defects. In particular, they are fertile and breed normally while Dock5 is expressed in testis and placenta, suggesting that Dock5 do not play an essential role in these tissues. Therefore, inhibiting Dock5 to limit bone resorption permits to have limited side effects on other physiological functions.

Figure 8:
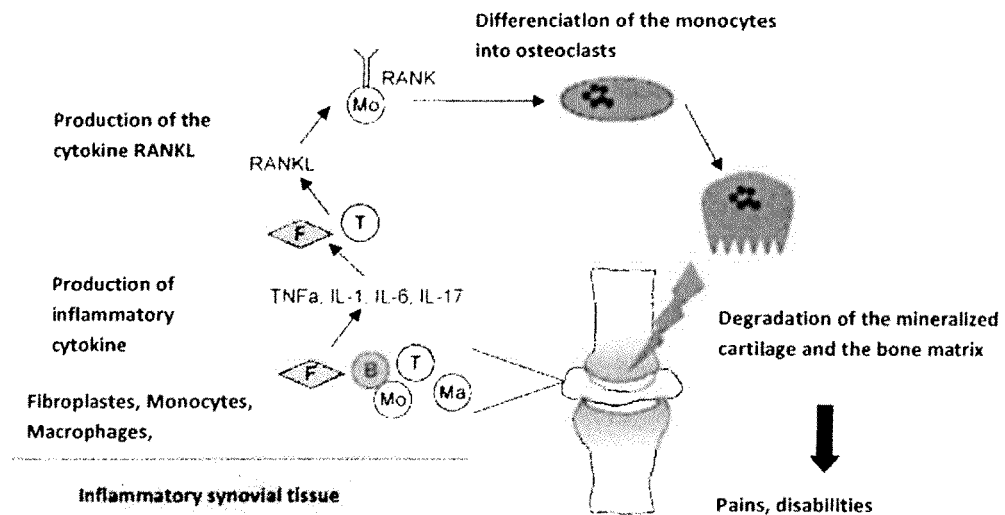
FIG. 8 shows the mechanism of the activation of osteoclasts by joint inflammation.

II. N-(3,5-Dichlorophenyl)benzene-sulfonamide Protects Mice from Arthritis-Induced Bone Loss In inflammatory arthritis pathologies such as rheumatoid polyarthritis, the inflammatory reaction in the synovial tissue causes differentiation of osteoclasts that destroy the bone in the area of the joints (see FIG. 8). The arthritis model induced by injecting bovine collagen into DBA1 mice is classically used as a model for this pathology.

II.a. Methodology

Protocol experiment 1: 2 naive DBA1 mice, 6 control mice injected with PBS and 8 test mice receiving the compound C21, 5 mg/d/kg, 5 days per week, as a retro-orbital sinus injection. The mice are distributed in 2 cages, with 1 naive mouse, 3 control mice and 4 test mice per cage. The animals, with the exception of the naive mice, receive an injection of 100 mg of bovine collagen at day 0 and at day 20.

Protocol experiment 2: 4 naive DBA1 mice, 12 control mice injected with PBS and 12 test mice receiving the compound C21, 15 mg/d/kg, 5 days per week, as an intraperitoneal injection. The mice are distributed in 2 cages, with 2 naive mice, 6 control mice and 6 test mice per cage. The animals, with the exception of the naive mice, receive an injection of 100 µg of bovine collagen at day 0 and at day 20.

II.b. Analysis

The arthritic score of each mouse is established twice per week between days 20 and D52, in order to measure swelling and deformation of the joints of the four limbs, an indication of the inflammatory response. The mice are sacrificed at D53, the legs are dissected and the structure of the bone surface of the metatarsi is imaged by micro-tomography in order to show the bone degradation at the area of the joints. The bone volume with respect to the total volume of the joint (BV/TV) decreases with the formation of resorption cavities. The measurements were performed on the joint of the central finger of the right metatarsus in experiment 1 and from the left and the right metatarsus in experiment 2. Anti-collagen IgG levels were measured in the serum of the mice in experiment 2 at day 52.

II.c. Results

Inflammation: C21 has No Effect on Inflammation

Figure 9:
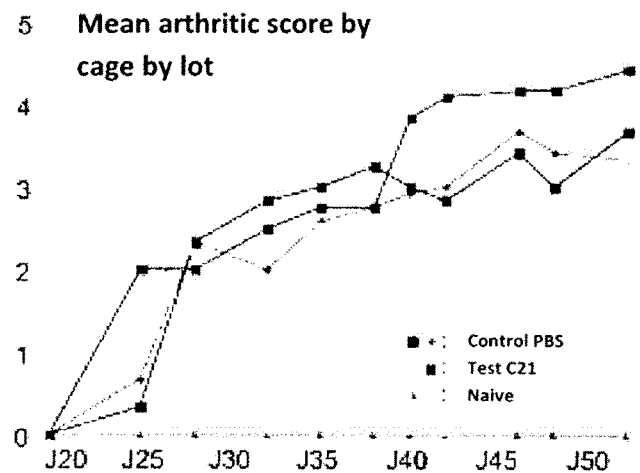
FIG. 9 shows the change in the mean arthritic score of each group of mice after the second collagen injection.

Experiment 1: C21 and PBS mice showed a similar inflammatory response (FIG. 9), with a mean arthritic score on D52 of 3.78±1.23 and 3.5±1.29, respectively. The naive mice showed no inflammatory signs (score 0).

Figure 10:
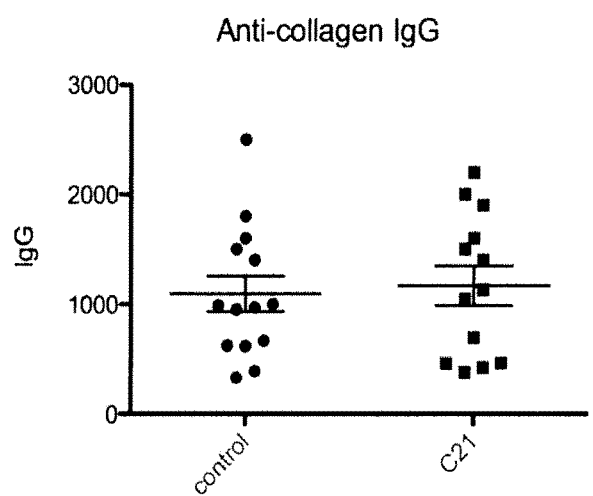
FIG. 10 shows the levels of anti-collagen IgGs in C21 and PBS.

Experiment 2: The C21 and PBS mice showed a similar inflammatory response and non-significantly different levels of anti-collagen IgGs (FIG. 10).

Bone Degradation: C21 Protects the Mice from Articular Bone Loss

Figure 11:
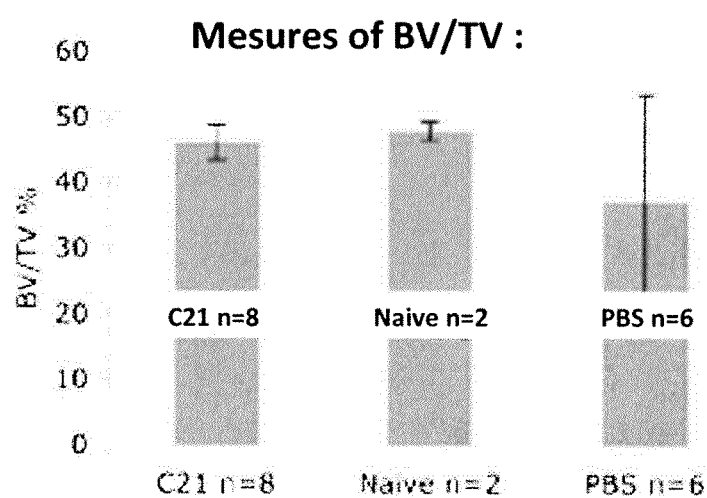
FIG. 11 shows the measurements of BV/TV: bone volume/total volume by micro-tomography on mice at the end of the experiment (D53).

Experiment 1:

The measurement of the bone mass (BV/TV: bone volume/total volume) by micro-tomography shows that the mice treated with C21 did not have any BV/TV modification by comparison with the naive mice, whereas a strong heterogeneity was observed in the PBS control mice (FIG. 11).

Figure 12:
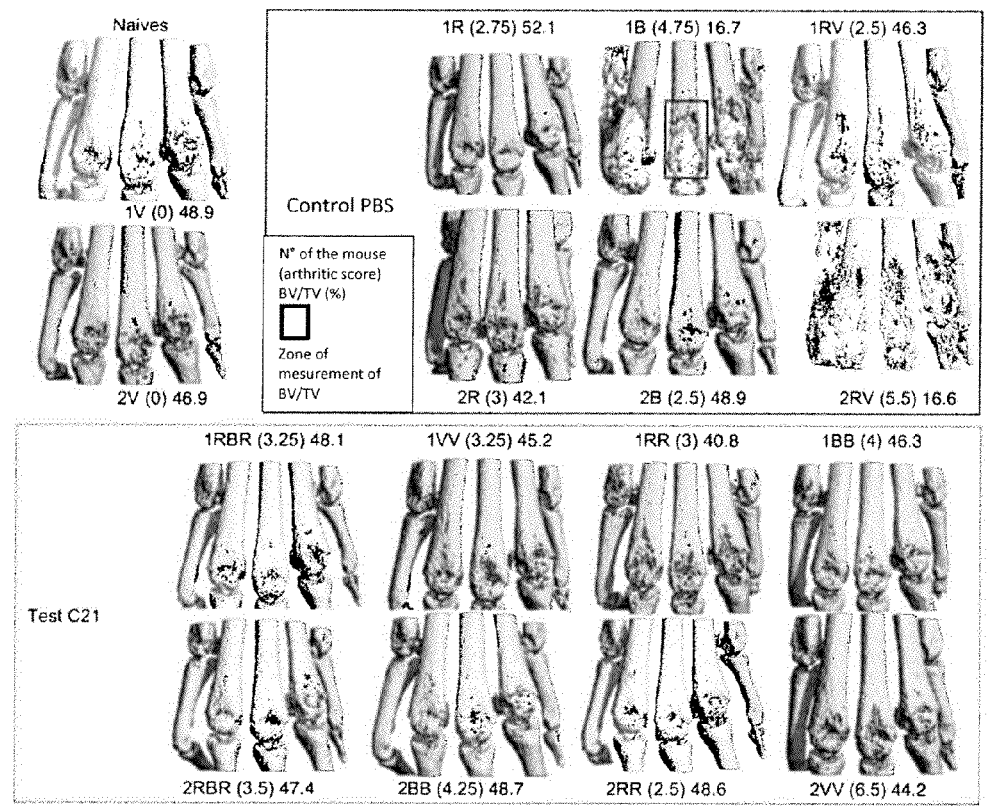
FIG. 12 shows the micro-tomography images of the first joint of the right metatarsus of the mice. These images are obtained after reconstruction of the micro-tomography cross-sections. For each mouse, the arthritic score at the end of the experiment is provided between parentheses and the BV/TV value measured for the same region for each mouse, indicated by the rectangle on 1 B, is provided.

A three-dimensional reconstruction of the first joint of the metatarsus was produced (FIG. 12). For the control group: observation of very significant bone degradation in 3 of the 6 PBS mice (1B, 2RV and 2R) and moderate degradation in 1 mouse (1RV), with 2 mice showing no sign of bone involvement (2B, 1R). With regard to the test group: only 1 C21 mouse (1RR) of the 8 showed moderate bone degradation. These different levels of degradation are reflected by the BV/TV measurements (number on the right-hand side for each joint in FIG. 12).

It should be noted that the PBS mice with a very strong inflammatory reaction (score≥4, 1B and 2RV) show massive bone degradation whereas in the C21 mice no correlation is observed between the arthritic score and BV/TV: the 1BB, 2BB and 2VV mice have a score greater than 4 but do not have any bone involvement.

Figure 13:
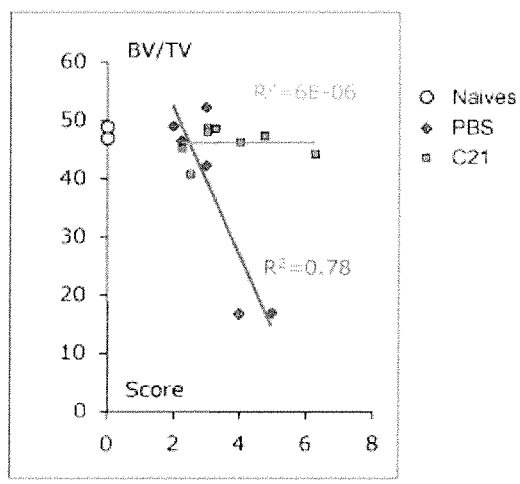
FIGS. 13 and 14 show the analysis of BV/TV as a function of the arthritic score. The graph indicates, for each mouse, its bone mass as a function of its arthritic score (Values in FIG. 4).

The analysis of the BV/TV relative to the arthritic score shows a negative correlation between BV/TV and the arthritic score for the PBS control mice (FIG. 13). This is what is expected: the inflammatory reaction causes articular bone loss. However, the mice treated with C21 show maintenance of their bone mass regardless of their arthritic score.

Figure 14:
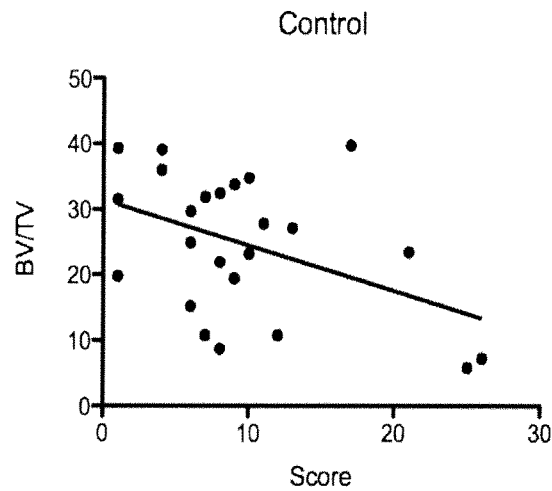
Figure 14:
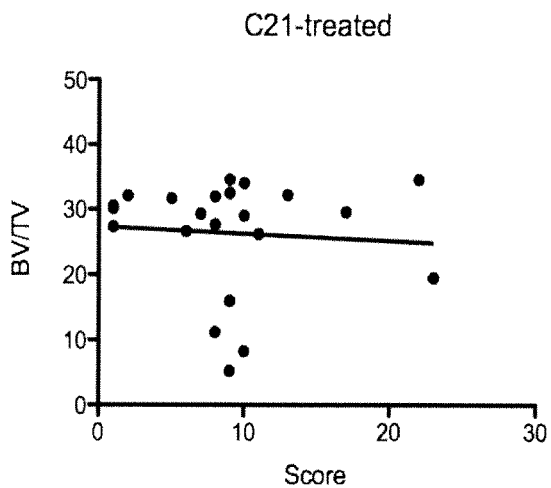

Experiment 2:

Similar to experiment 1, we found that the BV/TV of control mice was negatively correlated with the arthritic score whereas in there was no correlation between the BV/TV and the arthritic score in mice receiving C21 (FIG. 14).

Figure 15:
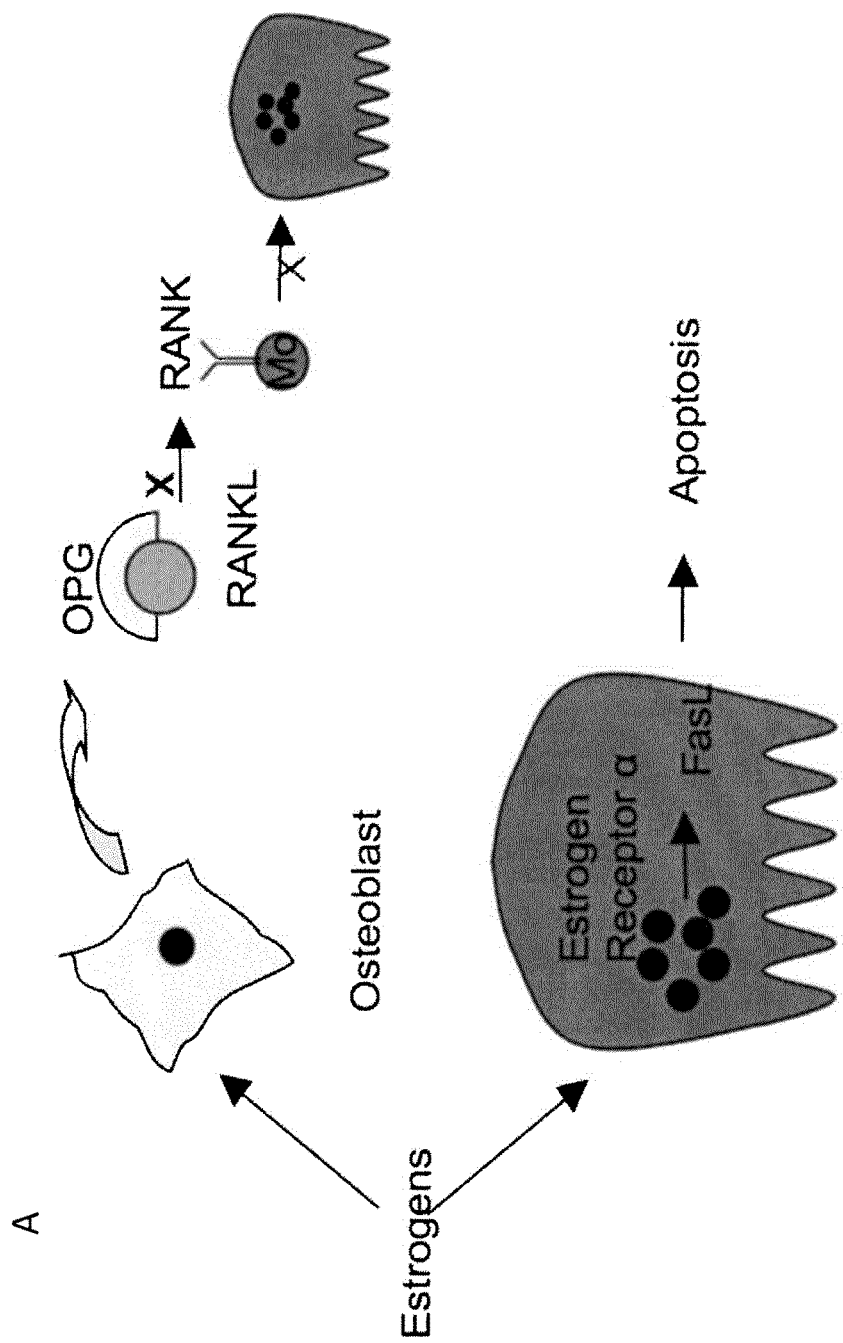
FIGS. 15A-15B show the mechanism of the activation of osteoclasts by the loss of estrogen expression after ovariectomy.
Figure 15:
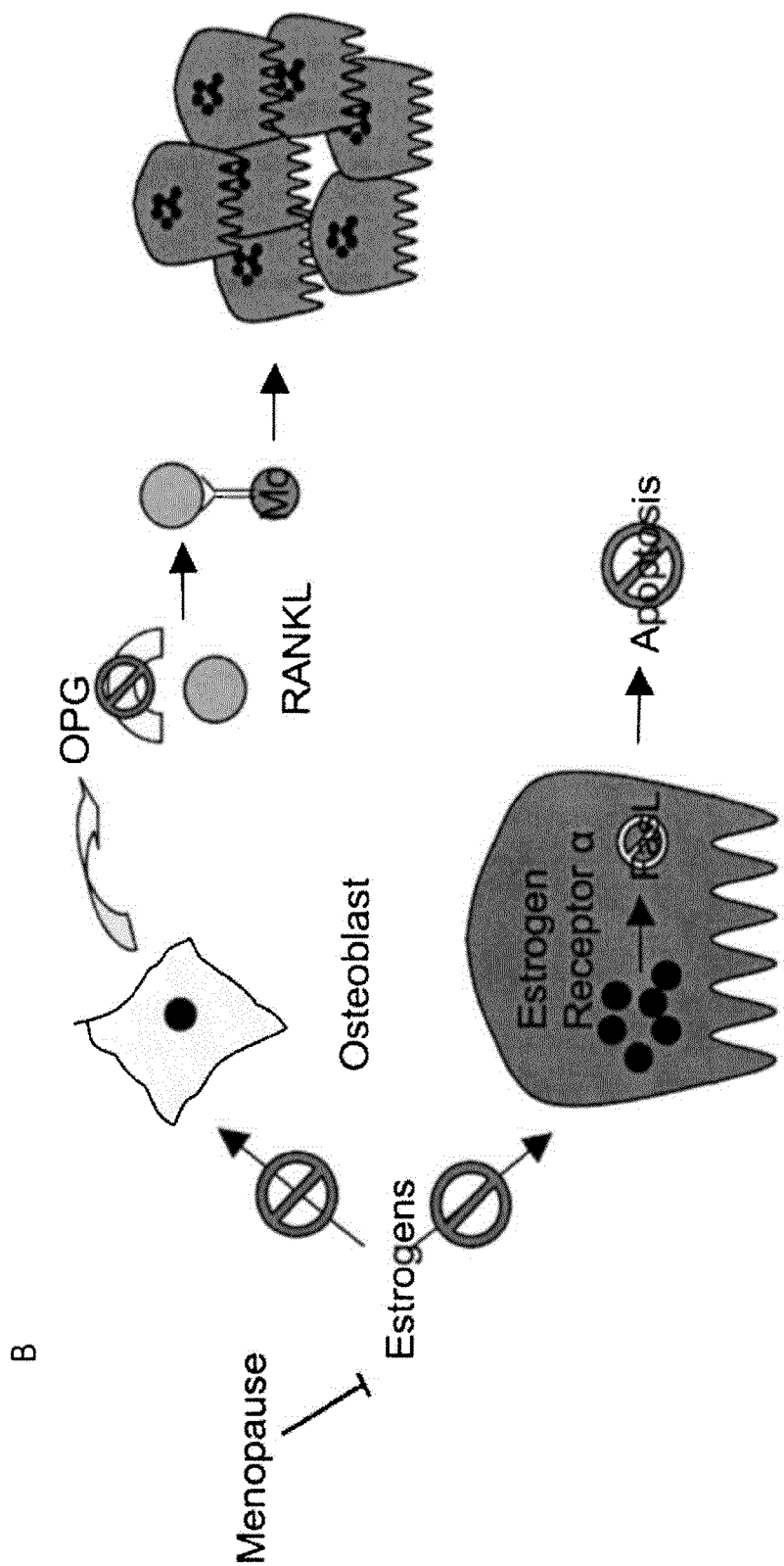

III. N-(3,5-Dichlorophenyl)benzene-sulfonamide Protects Mice from Ovariectomy-Induced Bone Loss After menopause, a decrease in bone density due to an increase in bone resorption, leading to osteoporosis, is observed. The decrease in estrogen secretion causes i) an increase in the osteoclast level due to the decrease in secretion of OPG, a RANKL inhibitor, by the osteoblasts and ii) an increase in the lifetime of the osteoclasts due to a decrease in the production of FasL, a promoter of apoptosis, by these cells. The ovariectomy model in the mouse is classically used as a model for this physiological disturbance (see FIG. 15).

III.a. Protocol

Protocol experiment 1: 8 C57B1/6 mice underwent ovariectomy (OVX) and 4 mice were operated on without ablation of the ovaries (SHAM). After this operation, 4 OVX mice received the C21 compound (test group), 5 mg/d/kg, 5 days per week for 28 days, as a retro-orbital sinus injection, and the other 4 OVX mice (control group) and the SHAM group received PBS.

Protocol experiment 2: 16 C57B1/6 mice underwent ovariectomy (OVX) and 15 mice were operated on without ablation of the ovaries (SHAM). After this operation, 8 OVX mice received the C21 compound (test group), 15 mg/d/kg solubilized in 100 µl of 5% EtOH and 4% solutol, 5 days per week for 28 days, as an intraperitoneal injection, and the other 8 OVX mice (control group) and the SHAM group received 100 µl of 5% ethanol/4% solutol vehicle solution.

III.b. Analysis

Figure 16:
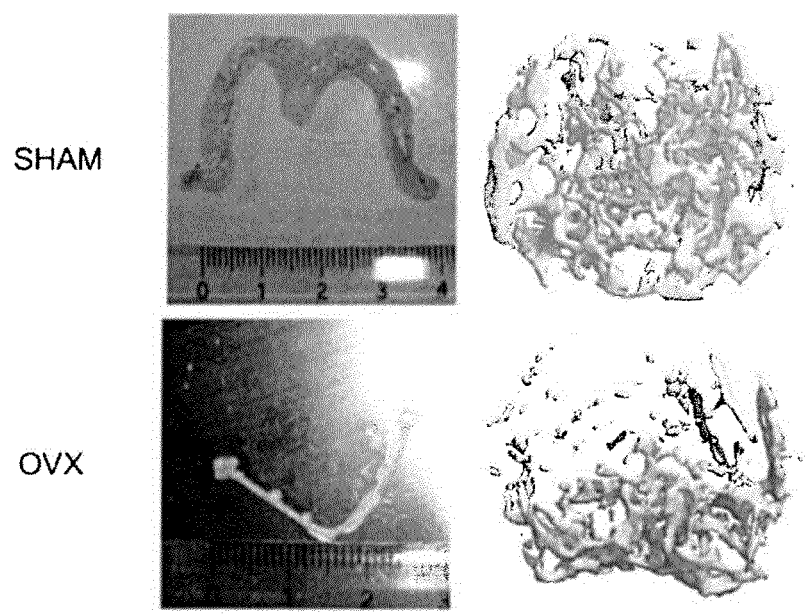
FIG. 16 shows the analysis of the bones of the mice following ovariectomy.

At the end of the protocol, D28 after operation, the mice are sacrificed. The uteri are dissected and weighed, and their atrophy is an indicator of the efficacy of the ovariectomy. The ovariectomy causes atrophy of the uterus of the mice with respect to mice not having undergone ovariectomy, which is accompanied by a strong decrease in the trabecular bone mass visible in the micro-tomography images. The legs are dissected and the structure of the trabecular bone mass (inside the bone) of the distal femur is imaged by micro-tomography in order to show bone degradation (FIG. 16).

III.c. Results

Figure 17:
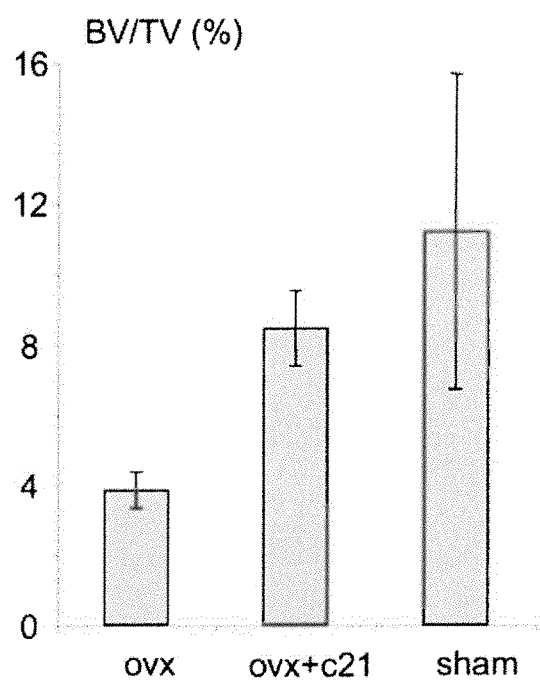
FIGS. 17 and 18 show the measurement of the BV/TV at the level of the right distal femur by micro-tomography.

The measurement of the BV/TV at the level of the right distal femur by micro-tomography shows a strong decrease in the bone mass of the mice having undergone ovariectomy with respect to the mice not having undergone ovariectomy. It is noted that the bone mass of the mice having undergone ovariectomy is not reduced when the mouse has received the C21 compound (see FIG. 17).

Figure 18:
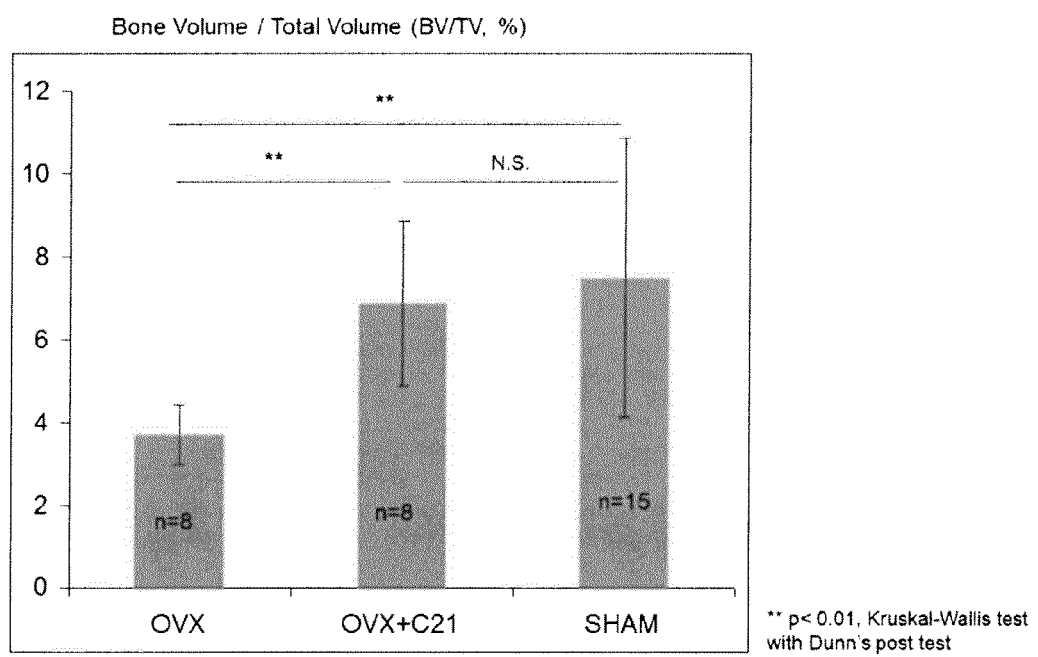

Experiment 2 again showed that ovariectomy provoked a strong bone loss in control OVX animals as compared to SHAM operated animals while C21 injected OVX animals retained a bone mass not significantly different from the SHAM animal (see FIG. 18).

Figure 19:
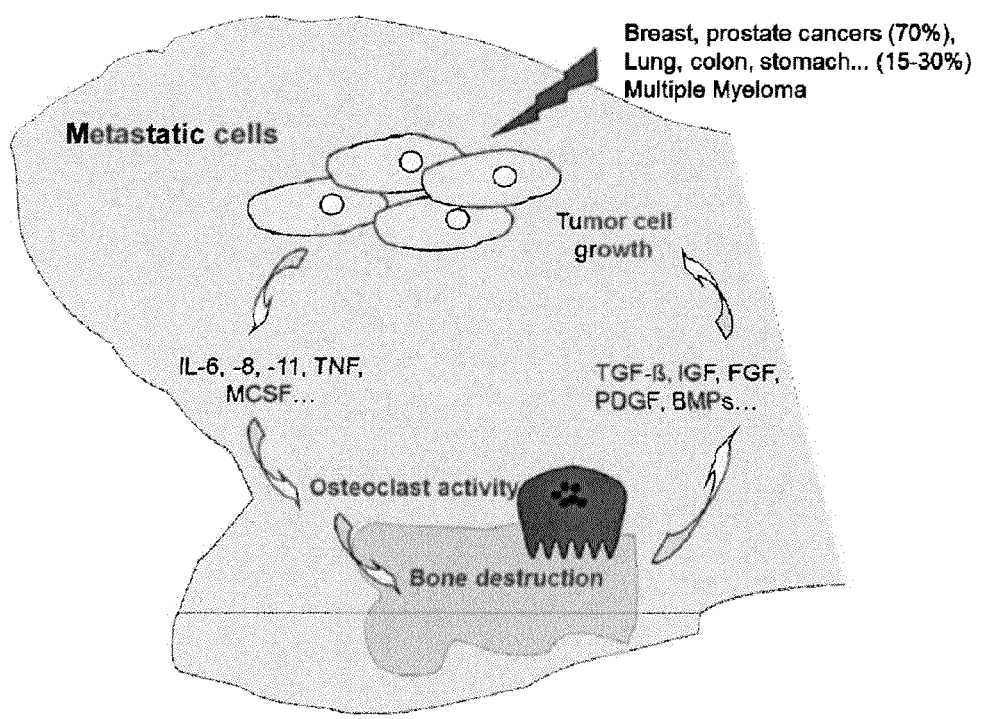
FIG. 19 shows the cycle of bone metastases where osteoclasts and metastatic cells stimulate each other's development.

IV. N-(3,5-Dichlorophenyl)benzene-sulfonamide Limits Bone Metastasis Growth in the Mouse The metastatic tumor cells in the bone matrix produce factors that directly or indirectly stimulate osteoclast differentiation and bone resorbing activity. In return, by resorbing it, the osteoclasts liberate growth factors embedded within the bone matrix that will stimulate the proliferation of metastatic cells. This results in the vicious cycle of bone metastases where osteoclasts and metastatic cells stimulate each other's development (FIG. 19). C21 being an efficient inhibitor of bone resorption, it was further assayed for its ability to slow down metastatic cell proliferation within the bone marrow. B16-F10 cells are derived from a C57B1/6 mouse melanoma and have a strong tropism for the bone. They are classically used as a model for bone metastases.

IV.a. Protocol

19 C57B1/6 mice received an injection of $10^5$ B16F10 melanoma cells expressing luciferase in the left ventricle, 9 mice received the C21 compound (test group), 15 mg/d/kg solubilized in 100 µl of 5% EtOH and 4% solutol, every days for 12 days, as an intraperitoneal injection, and the other 10 mice (control group) received 100 µl of 5% ethanol/4% solutol vehicle solution.

IV.b. Analysis

Figure 20:
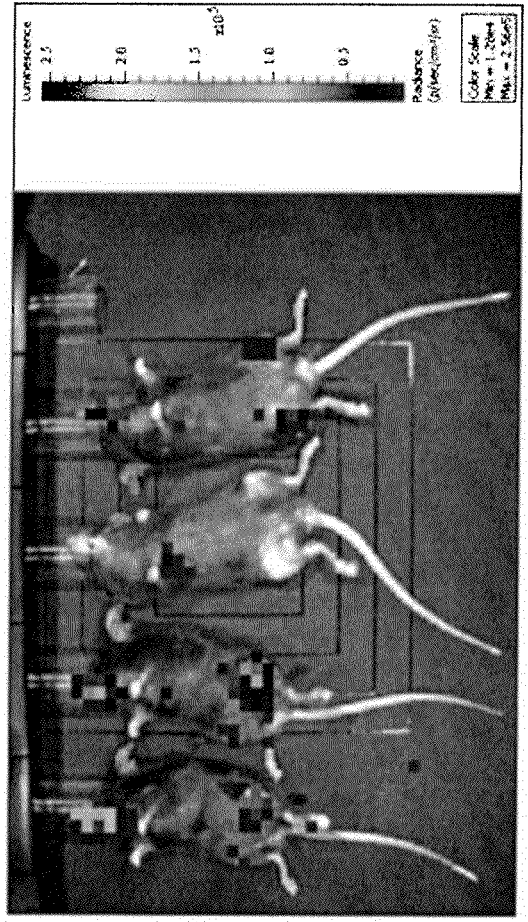
FIG. 20 shows the protocol of induction of bone metastases.

The proliferation of B16F10 cells was followed by their bioluminescence, measured at days 7, 10 and 12 after injection of the cells (FIG. 20).

IV.c. Results

Figure 21:
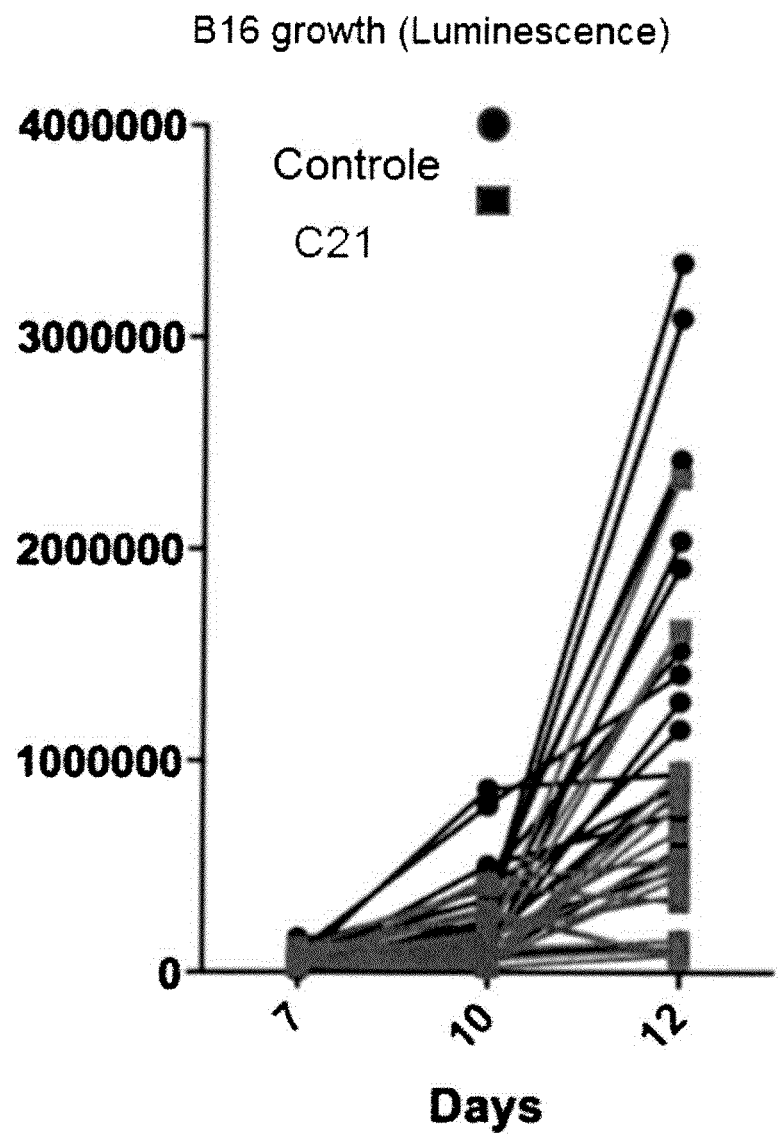
FIGS. 21A-21B show measurement of bioluminescence in the tibia of the mice the study the proliferation of B16F10 cells.
Figure 21:
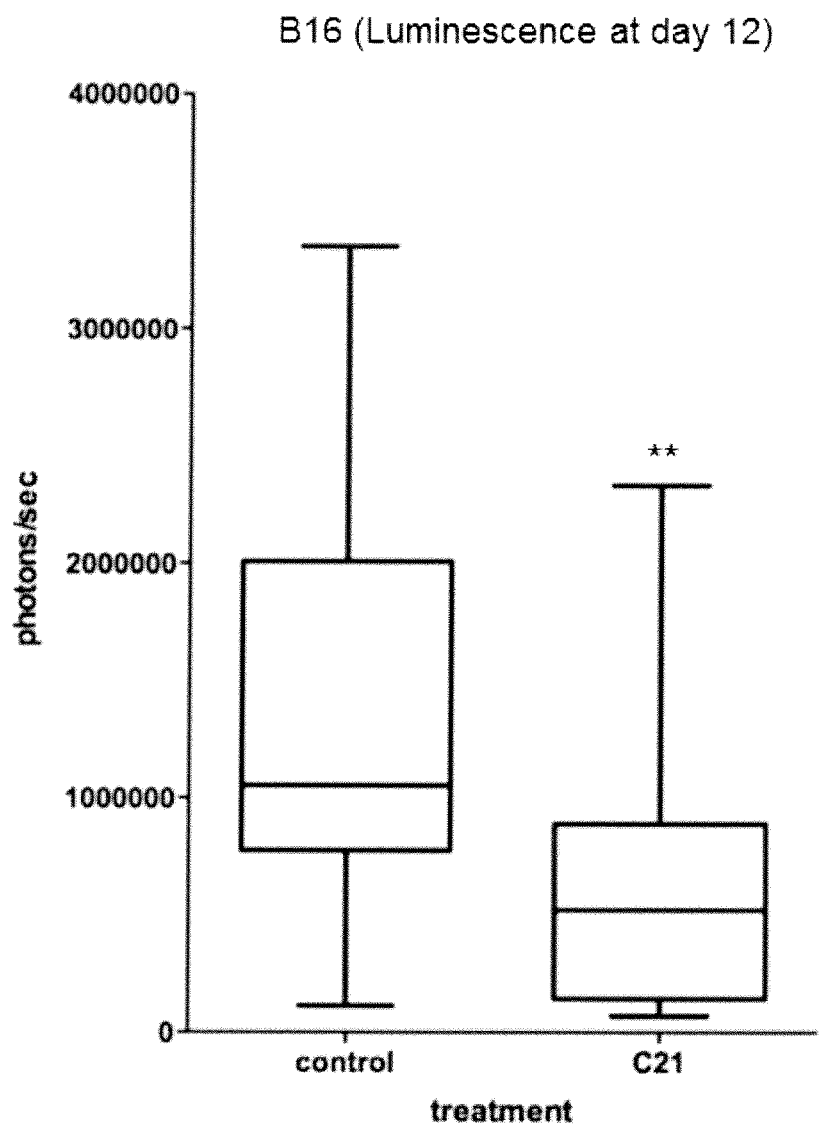

The measurement of bioluminescence in the tibia of the mice revealed a strong proliferation of B16F10 cells in control mice. It is to note that the proliferation of B16F10 cells was markedly slowed down in animals receiving C21 (FIG. 21).

CONCLUSION

The results above show that N-(3,5-Dichlorophenyl)benzene-sulfonamide makes it possible to protect mice from inflammation-induced articular bone loss and ovariectomy-induced trabecular bone loss. It also reduces the development of bone metastases.

The invention claimed is:

1. A method for treating a disease comprising the step of administrating an effective amount of N-(3,5-dichloro phenyl)benzenesulfonamide to a subject in need thereof,
wherein the disease is menopause, osteoporosis, osteopenia due to bone metastases, periarticular erosions in rheumatoid arthritis, primary hyperparathyroidistn, hypercalcemia of malignancy, Paget's disease of hone, periodontal disease, immobilization induced osteopenia or bone metastasis.

2. The method according to claim 1, wherein the disease is osteoporosis.

3. The method according to claim 1, wherein the subject is under a glucocorticoid treatment.

4. The method according to claim 1, wherein the subject is a postmenopausal woman.

5. The method according to claim 1, wherein the subject has bone metastases.

6. The method according to claim 1, wherein the subject is a mammal selected from the group consisting of: rodent, cat, dog, primate and human.

7. The method according to claim 1, wherein said N-(3,5-dichloro phenyl)benzenesulfonamide is administered at concentration from 2 mg/D/kg to 50 mg/D/kg.

8. A pharmaceutical composition comprising N-(3,5-dichloro phenyl)benzenesulfonamide, and, optionally, a pharmaceutically acceptable support.

* * * * *